(12) United States Patent
Kosinski et al.

(10) Patent No.: US 7,058,584 B2
(45) Date of Patent: Jun. 6, 2006

(54) APPARATUS AND METHOD FOR PROCESSING PRESCRIPTION REQUESTS USING A REMOTELY LOCATED PRESCRIPTION PROCESSING SYSTEM

(75) Inventors: Diana L. Kosinski, Whitehouse Station, NJ (US); Mark W. Sullivan, Morristown, NJ (US); Steven M. McNamara, West Milford, NJ (US); Melissa Russo, Oakland, NJ (US)

(73) Assignee: Medco Health Solutions, Inc., Franklin Lakes, NJ (US)

(*) Notice: Subject to any disclaimer, the term of this patent is extended or adjusted under 35 U.S.C. 154(b) by 0 days.

(21) Appl. No.: 10/055,968

(22) Filed: Jan. 28, 2002

(65) Prior Publication Data

US 2003/0144876 A1 Jul. 31, 2003

(51) Int. Cl.
*G06F 17/60* (2006.01)

(52) U.S. Cl. ................... 705/2; 379/106.02; 379/93.12; 705/22; 705/28

(58) Field of Classification Search ................ 705/2–3, 705/26, 28–29, 22; 235/385; 700/236; 379/93.12, 106.01–106.02, 22
See application file for complete search history.

(56) References Cited

U.S. PATENT DOCUMENTS

| | | | | |
|---|---|---|---|---|
| 4,766,542 A | * | 8/1988 | Pilarczyk | 705/3 |
| 4,958,280 A | * | 9/1990 | Pauly et al. | 705/3 |
| 5,597,995 A | * | 1/1997 | Williams et al. | 235/375 |
| 5,664,109 A | * | 9/1997 | Johnson et al. | 705/2 |
| 5,666,492 A | * | 9/1997 | Rhodes et al. | 705/3 |
| 5,671,282 A | * | 9/1997 | Wolff et al. | 713/179 |
| 5,737,539 A | * | 4/1998 | Edelson et al. | 705/3 |
| 5,758,095 A | * | 5/1998 | Albaum et al. | 705/2 |
| 5,771,657 A | * | 6/1998 | Lasher et al. | 53/55 |
| 5,845,255 A | * | 12/1998 | Mayaud | 705/3 |
| 5,883,370 A | * | 3/1999 | Walker et al. | 235/375 |
| 5,970,462 A | | 10/1999 | Reichert | 705/2 |
| 5,995,939 A | * | 11/1999 | Berman et al. | 705/3 |
| 6,004,020 A | * | 12/1999 | Bartur | 700/236 |
| 6,014,631 A | * | 1/2000 | Teagarden et al. | 705/3 |

(Continued)

FOREIGN PATENT DOCUMENTS

WO WO 01/09701 A1 * 2/2001

OTHER PUBLICATIONS

Oswald, Sharon and William Boulton, Obtaining Industry control; the case of the pharmaceutical distribution industry, California Management Review, Fall 1995, 38, 1, p. 138.*

(Continued)

*Primary Examiner*—Joseph Thomas
*Assistant Examiner*—Carolyn M. Bleck
(74) *Attorney, Agent, or Firm*—Irah H. Donner; Wilmer Cutler Pickering Hale and Dorr LLP.

(57) ABSTRACT

An apparatus and method are disclosed for processing phone-in prescription requests. The apparatus is in the form of a prescription processing network that includes a prescription processing system and a communication device remotely located from the prescription processing system. The communication device is used to establish a communication channel with the prescription processing system and submit a prescription request over the communication channel. A pharmacist, associated with the prescription processing system, prepares a completed prescription form based, at least in part, on the submitted prescription request. The prescription processing network also includes a pharmacy for receiving the completed prescription form, and filling the prescription request based on the completed prescription form.

71 Claims, 24 Drawing Sheets

U.S. PATENT DOCUMENTS

| | | | |
|---|---|---|---|
| 6,112,182 A * | 8/2000 | Akers et al. | 705/2 |
| 6,202,923 B1 * | 3/2001 | Boyer et al. | 235/375 |
| 6,263,259 B1 * | 7/2001 | Bartur | 700/240 |
| 6,330,491 B1 * | 12/2001 | Lion | 700/237 |
| 6,397,190 B1 * | 5/2002 | Goetz | 705/3 |
| 6,493,427 B1 * | 12/2002 | Kobylevsky et al. | 379/67.1 |
| 6,529,801 B1 * | 3/2003 | Rosenblum | 700/237 |
| 6,564,121 B1 * | 5/2003 | Wallace et al. | 700/231 |
| 6,636,780 B1 * | 10/2003 | Haitin et al. | 700/236 |
| 6,680,999 B1 * | 1/2004 | Garcia | 379/88.22 |
| 6,711,460 B1 * | 3/2004 | Reese | 700/216 |
| 6,744,862 B1 * | 6/2004 | Kobylevsky et al. | 379/88.16 |
| 6,804,654 B1 * | 10/2004 | Kobylevsky et al. | 704/275 |
| 2002/0052760 A1 * | 5/2002 | Munoz et al. | 705/2 |

OTHER PUBLICATIONS

CVS and Merck-Medco form strategic alliance for Internet and Specialty Pharmacy Services, Business Wire, New York, Oct. 6, 1999, p. 1.*

U.S. Appl. No. 60/299,116, filed Jun. 18, 2001, Reese.*

RX SCAN: Imaging System helps process prescriptions, Drug Topics, Nov. 7, 1994, p. 70, File 9 #03631805.*

Felkey, BG and BI Fox, How do you spell relief: in store automation or central fill and central processing?, California Pharmacist, 2002, vol. 49, pp. 36-37.*

Vavra, Bob, Is Central Fill the Right RX?, Supermarket Business, Jul. 15, 2001, vol. 56 No. 7, p. 27.*

Medco website, Our products and services, accessed Oct. 13, 2004.*

* cited by examiner

COMPUTER

COMPUTER CONCEPTUAL

FLOW OF POTENTIAL
COMPUTER PROCESS

CONCEPTUAL VIEW OF
MEMORY STORAGE MEDIUM

APPARATUS AND METHOD FOR PROCESSING PRESCRIPTION REQUESTS USING A REMOTELY LOCATED PRESCRIPTION PROCESSING SYSTEM

BACKGROUND OF THE INVENTION

1. Technical Field

The present invention relates to processing prescription requests and, more particularly, to an apparatus and method for processing prescription requests submitted by physicians via, for example, a telephone or other remote device.

2. Description of the Related Art

Patients often require medication during the course of receiving health care services. The medication typically cannot be purchased over the counter, and must be prescribed by a physician. The physician must also determine an appropriate therapy for the medication. The therapy can include, for example, selection of the appropriate medication (or drug), medication strength, and dosage. The therapy must also be varied based on the individual patient. For example, consider two patients who are suffering from the same illness. The therapy for the first patient may not be appropriate for the second patient due to various physical differences such as age, weight, prior medical history or condition, etc.

Next, the physician must prepare a prescription request which contains all the necessary information regarding the therapy. This can be done, for example, manually or telephonically. Manual preparation requires writing the information on a prescription form. The patient then submits the prescription form to a pharmacist, who subsequently fills the prescription (i.e., prepares the medication). This process, however, can be very time-consuming and problematic for patients that require immediate dosages of the medication.

In order to at least minimize the amount of time required before a patient can receive the prescribed medication, physicians often place a telephone call to the pharmacy and submit the prescription request telephonically. The prescription request would then be filled by the pharmacist and the medication subsequently retrieved by the patient. This would eliminate, or at least reduce, the amount of time which the patient must wait for the medication.

We have determined that there are various problems associated with telephone prescription requests. First, the prescription request must be submitted to a registered pharmacist. Thus, the pharmacist is interrupted from the preparation of other prescription requests. These interruptions can result in significant increases in the amount of time required to fill all the prescription requests received at the pharmacy. The interruptions also add to operational costs because additional pharmacist time is required to fill the prescription requests. Furthermore, the physician must interrupt scheduled patient examinations in order to contact the pharmacy and submit the prescription request. There are other times, for example, when it is more convenient for a physician to designate a predetermined time interval to contact a pharmacy and submit multiple prescription requests. Although convenient to the physician, such a solution may not be beneficial to the pharmacist.

No solution currently exists to address these problems; namely, providing a cost-effective and efficient way to submit an audible prescription request. There exist, however, various methods and systems that address other prescription related needs of physicians and pharmacists.

For example, U.S. Pat. No. 5,883,370, incorporated herein in its entirety by reference thereto, discloses an automated method for filling drug prescriptions. The method attempts to verify a match between the doctor's prescription form and the drug selected from the pharmacy's inventory to fill the prescription. While effective at ensuring that the proper drug has been dispensed, the method of the '370 patent does not address the problems associated with submitting prescription requests and processing the prescriptions for use by patients.

U.S. Pat. No. 5,970,462, incorporated herein in its entirety by reference thereto, discloses an on-line pharmacy automated refill system. The '462 patent provides a limited ability to receive and process certain prescription information over the telephone. However, the system disclosed in the '462 patent is limited in use to refills of prescriptions. There is no ability to submit an original prescription request or make changes to the therapy during refill, as these actions require intervention from a physician.

U.S. Pat. No. 5,666,492, incorporated herein in its entirety by reference thereto, discloses a flexible computer based pharmaceutical care cognitive services management system and method. The system of the '492 patent provides various benefits to physicians and pharmacists. However, it does not address certain problems associated with processing prescription requests such as processing new prescriptions.

In addition, existing systems, while capable of addressing numerous prescription-related needs, simply do not provide a cost-effective and efficient ability to submit and process specialized prescription requests such as, for example, audible prescription requests.

Accordingly, there exists a need for a prescription processing network capable of receiving specialized prescription requests such as audible prescription requests.

There also exists a need for a prescription processing network that accepts audible changes in prescription therapy.

There exists a further need for a prescription processing network which allows a physician to conveniently submit audible prescription requests.

There exists a still further need for a prescription processing network capable of receiving audible prescription requests without interrupting a pharmacist from preparing existing prescriptions.

SUMMARY OF THE INVENTION

It is therefore one feature and advantage of the present invention to address at least some of the shortcomings of the prior art in receiving and processing prescription requests.

It is another optional feature and advantage of the present invention to provide a prescription processing network capable of receiving specialized prescription requests, such as audible, facsimile, and email prescription requests.

It is yet another optional feature and advantage of the present invention to provide a prescription processing network that accepts changes in prescription therapy.

It is a further optional feature and advantage of the present invention to provide a prescription processing network which allows a physician or qualified personnel to conveniently submit prescription requests in various forms and using various devices such as, audible, facsimile, email, etc.

It is a still further optional feature and advantage of the present invention to provide a prescription processing network capable of receiving prescription requests in various formats without interrupting a pharmacist from the preparation existing prescriptions.

The foregoing, and various other needs, are addressed, at least in part, by the present invention, wherein a prescription processing network receives specialized prescription requests, such as audible, facsimile, or email prescription requests for efficient processing by a pharmacist, or personnel capable of independently assessing correctness of the prescription request, at a convenient or predetermined time.

According to one embodiment of the invention, a method of processing prescription requests is provided. The method comprises the steps of: establishing a connection to a remotely located prescription processing system; submitting a prescription request to the prescription processing system; preparing, by personnel capable of independently assessing correctness of the prescription request, a completed prescription form based on the submitted audible prescription request; sending the completed prescription form to a filling pharmacy; and filling the prescription request, at the filling pharmacy, based on the completed prescription form.

Such a method has an advantage of improving the efficiency of a physician's clinic and/or a pharmacist's ability to prepare prescription requests. Thus, cost savings can be realized. For example, a physician does not have to interrupt scheduled patient examinations in order to prepare prescription requests. Instead, the physician can simply select a convenient time to submit one or more prescription requests. In addition, the pharmacist does not have to interrupt the preparation of a prescription in order to receive a new prescription request from the physician. Hence, prescriptions can be prepared more efficiently and with less likelihood of error because the pharmacist can work uninterrupted. Furthermore, there are times when the physician is unable to reach the pharmacist in order to submit the prescription request. The present invention eliminates, or at least reduces, the amount of time consumed by the physician while trying to reach the pharmacist.

The present invention optionally provides an ability to submit the prescription request in various formats. The submitted prescription request can be in an audible form using, for example, a conventional telephone, a mobile telephone, or a microphone operatively coupled to a computer. The mobile telephone can be either cellular, digital, satellite, etc. The submitted prescription request can optionally be in the form of an electronic mail or data received from a mobile device such as a two-way pager or personal digital assistant (PDA). Furthermore, the prescription form may be completed by various individuals. More particularly, the prescription form may be completed, for example, by a pharmacist, a medical doctor, a licensed physician assistant, etc. who is capable of reviewing the prescription request to independently interpret its content and assess its correctness.

According to an optional feature or aspect of the present invention, the prescription request is captured and subsequently transcribed before the pharmacist prepares the completed prescription form. Furthermore, the captured prescription request can be converted to a digitized format and stored in a database of the prescription processing system. The digitized format can correspond to various formats including, for example, ASCII, formatted text, Microsoft™ Word™, WordPerfect™, standard facsimile formats, standard wireless transmission formats, etc. Additionally, the digitized format can optionally correspond to standard digitized audio formats such as the ".wav" format. Such a configuration provides the flexibility of maintaining records of prescription requests that are received by the prescription processing system. Also, the digitized prescription request can be easily transmitted to different individuals using, for example, electronic mail (email) systems. This can allow verification of the transcription based on the original prescription request.

Another optional feature of the present invention requires that the person submitting the prescription request (e.g., the physician or other qualified personnel) be prompted to submit certain information. This can include, for example, information regarding the physician, the member whose insurance carrier providing coverage for the prescription, and the patient receiving the prescription. The physician information can include the physician's name, office address and telephone number, and DEA number. The member information can include the member's name, address, and insurance identification number. The patient information can include the patient's name, age, medical condition, other medications being taken, etc. Hence, the present invention allows for significantly more detailed information than can be written on a conventional prescription form. One advantage of such an embodiment is that the detailed information can allow multiple personnel to review the prescription request in order to minimize possible adverse drug interactions, allergic reactions, etc.

Other optional aspects of the present invention allow the physician to indicate whether or not the prescription request is a renewal. Thus, it would not be necessary to repeat all of the details of the prescription request. Rather, the physician could simply submit the original prescription number. The present invention also allows the physician to change the medication therapy for the patient. For example, depending on prior consultation, the physician may decide to reduce or increase the dosage of a particular medication.

According to another optional embodiment of the present invention, a method is provided for submitting a prescription request and allowing a patient (or authorized personnel) to retrieve a filled prescription based on the prescription request. The method comprises the steps of: initiating a connection to a remotely located prescription processing system; submitting a prescription request to the prescription processing system; and retrieving, by the patient, a filled prescription from a predetermined filling pharmacy remotely located from the prescription processing system. According to such a method, a physician can submit one or more prescription requests without having to interrupt scheduled patient examinations or directly contacting a pharmacist.

According to another optional embodiment of the present invention, a method is provided for processing a submitted prescription request. The method comprises the steps of: receiving a request from a remote source to establish a connection with a local prescription processing system; establishing a connection with the remote source; receiving a prescription request; preparing, by personnel capable of independently assessing correctness of the prescription request, a completed prescription form based on the prescription request; and sending the completed prescription form to a filling pharmacy to be filled. It should be noted that the request to establish a connection can take many forms, including a telephone ring that must be answered, an email message that must be acknowledged, etc. Such an embodiment allows the pharmacist to efficiently prepare prescriptions without interruptions from a physician to receive new prescription requests. Accordingly, overall efficiency can be improved while reducing possible errors.

According to another optional embodiment of the present invention, a prescription processing network is provided. The prescription processing network includes a prescription processing system and a communication device remotely located from the prescription processing system. The communication device is used to establish a communication channel with the prescription processing system and submit a prescription request over the communication channel. A pharmacist, associated with the prescription processing system, prepares a completed prescription form based, at least in part, on the submitted prescription request. The prescription processing network also includes a pharmacy for receiving the completed prescription form, and filling the prescription request based on the completed prescription form. Such a prescription processing network can improve both the efficiency of a physician's clinic and a pharmacist's ability to prepare prescription requests. The physician can select a convenient time and submit one or more prescription requests without interrupting the pharmacist from preparing other prescriptions.

According to an optional embodiment of the present invention, a method is provided for submitting a prescription request wherein a filled prescription can be subsequently retrieved by a patient. A connection is first initiated to a remotely located prescription processing system. Next, an audible prescription request is submitted to the prescription processing system. The patient subsequently retrieves a filled prescription from a predetermined filling pharmacy remotely located from the prescription processing system. Such a method provides an efficient manner of submitting prescription requests.

According to another optional embodiment of the present invention, a method is provided for processing a submitted prescription request. A local prescription processing system establishes a connection with a remote source upon receiving a request from the remote source to establish a connection. An audible prescription request is then received by the prescription processing system. A pharmacist, or other personnel capable of independently assessing correctness of the prescription request, prepares a completed prescription form based, at least partially, on the audible prescription request. Finally, the completed prescription form is sent to a remotely located pharmacy to be filled. Such a method eliminates, or at least minimizes, interruptions to the pharmacist who will ultimately prepare the prescription.

Another optional embodiment of the present invention provides a method of processing prescription requests wherein a connection is established to a remotely located system and an audible prescription request is submitted to the remotely located system. A pharmacist, or personnel capable of independently assessing correctness of the prescription request, prepares a completed prescription form based, at least partially, on the submitted prescription request. The completed prescription form is then sent to a pharmacy where it is filled, based on the completed prescription form. The prescription request can optionally be provided in electronic form instead of audible form. For example, the prescription request can be in the form of a facsimile transmission, email transmission, wireless device transmission, electronic data transmission, etc.

According to another optional embodiment of the present invention, a prescription processing network includes a prescription processing system and a communication device remotely located from the prescription processing system. The communication device is useable for establishing a communication channel With the prescription processing system and submitting a prescription request over the communication channel. The prescription processing system is accessible by a pharmacist, or personnel capable of independently assessing correctness of the prescription request, in order to prepare a completed prescription form based, at least in part, on the submitted prescription request. The completed prescription form is then sent to a pharmacy where the prescription request can be filled based on the completed prescription form.

There has thus been outlined, rather broadly, the more important features of the invention and several, but not all, embodiments in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These, together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

DETAILED DESCRIPTION OF THE INVENTION

Figure 1:
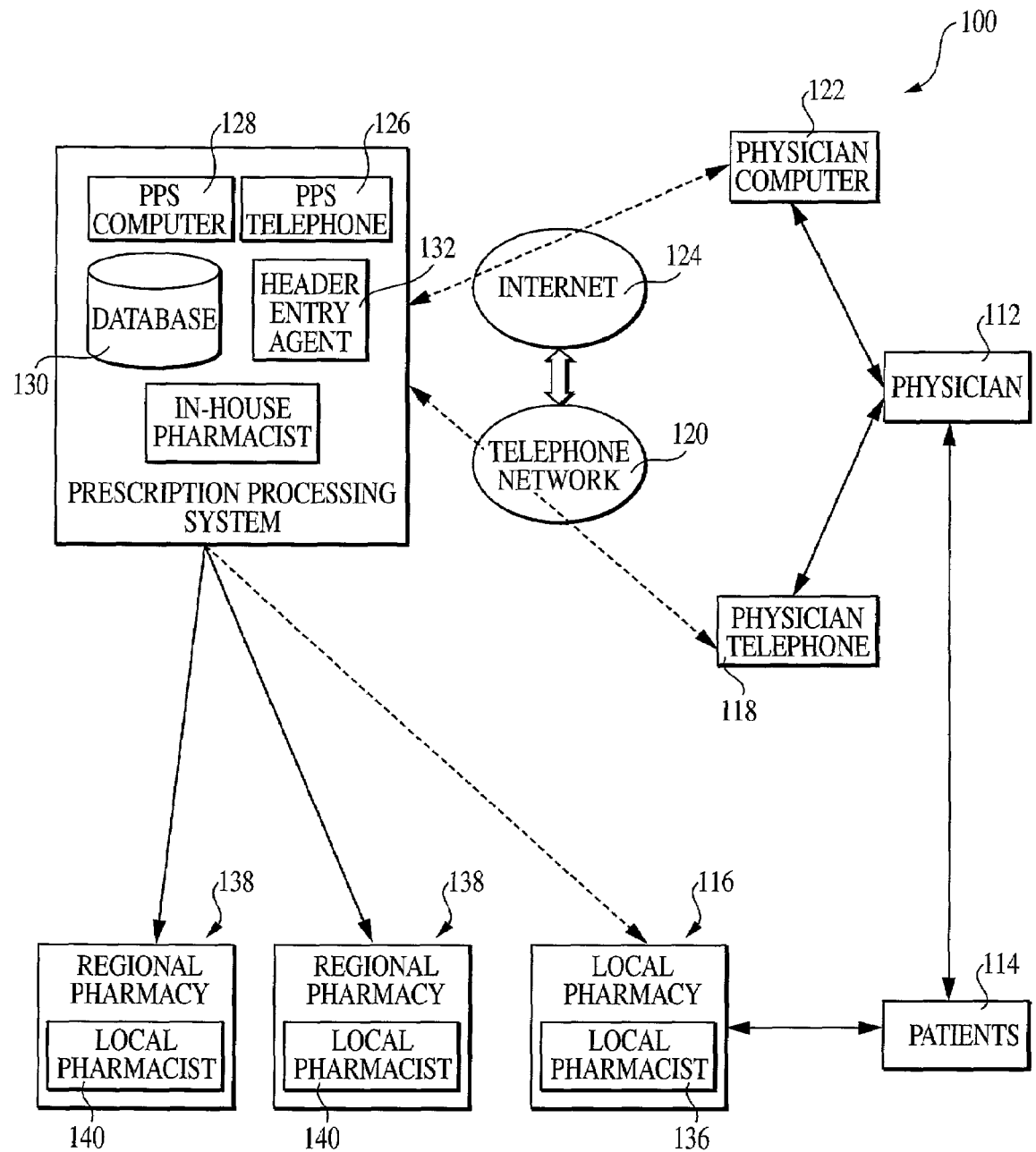
FIG. 1 is a block diagram illustrating a prescription processing network according to an exemplary embodiment of the present invention.

Reference now will be made in detail to the presently preferred embodiments of the invention. Such embodiments are provided by way of explanation of the invention, which is not intended to be limited thereto. In fact, those of ordinary skill in the art may appreciate upon reading the present specification and viewing the present drawings that various modifications and variations can be made.

For example, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

Prior to describing the details of the invention, a brief discussion of some of the notations and nomenclature used in the description will be presented. Next, a description of exemplary hardware useable in practicing the invention will be presented.

Notations and Nomenclature

The detailed descriptions which follow may be presented in terms of program procedures executed on a computer or network of computers. These procedural descriptions and representations are the means used by those skilled in the art to most effectively convey the substance of their work to others skilled in the art.

A procedure is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are preferably machine operations, although the operations may also be manual in alternative embodiments. Useful machines for performing the operation of the present invention include general purpose digital computers or similar devices.

The present invention also relates to apparatus for performing these operations. This apparatus may be specially constructed for the required purpose or it may include a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove more convenient to construct more specialized apparatus to perform the required method steps. The required structure for a variety of these machines will appear from the description given.

Prescription Processing Network

FIG. 1 is a block diagram illustrating an exemplary hardware configuration for a prescription processing network (PPN) 100 according to one embodiment of the present invention. The prescription processing network 100 includes a prescription processing system (PPS) 110 that receives and processes prescription requests using various standard equipment. The prescription requests can be in various forms including, but not limited to, voice (e.g., audible), facsimile, email, data and/or voice from a wireless/mobile device such as a mobile phone, two-way pager, personal digital assistant (PDA), etc. For example, if the prescription request is in audible form, processing can be handled via standard voice response units, and the like. As used herein, prescription requests refer to the information submitted by a physician 112 to identify a particular medication and dosage for a patient 114. During the course of regular medical consultation, patients 114 interact with his or her physician 112 in order to diagnose and possibly consider various treatment options where necessary. Frequently, the selected treatment requires use of prescribed medications and/or narcotics. The medication is not maintained at the physician's office, although, there are times when promotional samples may be available. Physicians can also maintain a supply of certain common drugs for immediate dispensing.

According to the disclosed embodiment of the invention, the physician 112 does not prepare a traditional prescription form that must be taken to a filling pharmacy, such as local pharmacy 116, by the patient 114. As previously discussed, such a procedure can be costly and very time consuming. Rather, the physician 112 submits an audible prescription request directly to the prescription processing system 110. As illustrated in FIG. 1, there are, for example, two options for submitting the prescription request. It should be noted, however, that the two options shown in FIG. 1 are only exemplary, and various other arrangements can be used to submit prescription request by the physician 112. For example, electronic systems such as facsimile devices or computer controlled peripherals can be used. In the description that follows, the prescription request will be frequently referred to as an audible prescription request. This is merely intended to assist in understanding the exemplary embodiment being described. As previously indicated, the prescription request can be in various formats. Furthermore, according to other embodiments of the invention, it may not be necessary for the physician 112 to submit the audible prescription request. Rather, arrangements can be made to have authorized personnel submit the audible prescription request instead of the physician 112.

For example, the physician 112 can write traditional prescriptions forms, while the authorized personnel submit multiple audible prescription requests to the prescription processing network 100, based on the prescriptions forms written by the physician 112. Such an arrangement has an advantage of minimizing the number of interruptions to both the physician 112 and the pharmacist, thus contributing to improved efficiency. Furthermore, prescription requests can be submitted via facsimile to the prescription processing system 110. Additional embodiments utilizing a facsimile will be described in greater detail hereinbelow. Again, it should be appreciated that the physician computer 122 and facsimile device represent different devices for transmitting the prescription request electronically. Accordingly, various other types of electronic communication devices can be used to transmit the prescription request.

According to the embodiment of the invention illustrated in FIG. 1, the physician 112 has an option of connecting to the prescription processing system 110 using a regular telephone, such as physician telephone 118. Using this process, a connection is established over the local, or other appropriate, telephone network 120. As is well known, such a process requires dialing the telephone number corresponding to the prescription processing system 110. Once connected, the physician 112 verbally submits the audible prescription request.

Alternatively, as shown in FIG. 1, the physician 112 can submit the prescription request through a conventional computer (e.g., desktop, laptop, workstation, terminal, etc.), such as physician computer 122. According to such an embodiment, the physician computer 122 would be necessarily equipped with an appropriate voice input device (not shown) and communication hardware/software to establish a connection over a packet-switched network such as the Internet 124. It should also be noted that the network connection need not be packet-switched. Any appropriate data transfer protocol/interface (e.g., Kermit, X-modem, serial, USB, TCP/IP, etc.) can be used. The connection to the Internet 124 can be established in many ways, including through the use of a modem (not shown) that establishes a connection to a local Internet service provider (ISP) (not shown) over the telephone network 120. Thus, data can pass through both the Internet 124 and the telephone network 120. Furthermore, as previously indicated, various other devices such as, for example, a PDA, facsimile, two-way pager, or mobile/wireless telephone can be optionally used by the physician to submit the prescription request.

The prescription processing system 110 includes various standard hardware and software for establishing a connection with the physician 112. For example, according to one embodiment of the present invention, the prescription processing system 110 can include a standard PPS telephone 126 and a standard PPS computer 128 configured with appropriate hardware and software to implement the present invention. The prescription processing system 110 can also include a database 130, a header entry agent 132, and an in-house pharmacist 134. The database 130 can be used to store and provide access to information while processing the prescription request. The header entry agent 132 verifies at least some of the data received and stored in the database 130. The in-house pharmacist 134 also verifies some of the data stored in the database 130 and prepares an actual prescription form. As previously stated, the PPS telephone 126 and PPS computer 128 are used to maintain the connection established by the physician 112 in order to receive the audible, or facsimile, prescription request.

While FIG. 1 illustrates a single database 130, PPS computer 128, PPS telephone 126, header entry agent 132, and in-house pharmacist 134, it should be noted that these are not limitations to the prescription processing system 110. Rather, multiple components of each can be provided to function as a whole subpart of the prescription processing system 110. In other words, many individual databases can be integrated to function as the database 130 illustrated in FIG. 1. Similarly, the prescription processing system 110 can include many individual PPS telephones 126, many header entry agents 132, many in-house pharmacists 134, etc.

In connection with the specific embodiment of the invention being implemented, various additional options are also available. For example, a telephone coupled to an appropriate standard voice messaging system (not shown) can be used to receive the call and guide the physician 112 through a series of menus. The menus can be accessed, or navigated, using a touch tone telephone keypad. Further embodiments of the invention provide an ability to incorporate voice response capabilities to the voice messaging system. Thus, the menus could be navigated using voice commands/responses from the physician 112. As the physician 112 is guided through the menus, the voice messaging system would prompt the physician 112 to input (e.g., speak, transmit, etc.) all necessary information, and record the information (either in digital or analog format) for later processing. Additionally, embodiments of the invention can include real-time lookup capabilities that retrieve information while receiving input from the physician 112. For example, when the physician begins to submit information regarding a patient 114, the patient's data file is retrieved as soon as a positive match can be made to the patient 114. This can be done in various ways including, for example, real-time (and possibly repetitive) query submissions to the database 130 based on incremental information (e.g., query terms) received from the physician 112.

Alternatively, the PPS computer 128 can be used to maintain the connection with the physician's computer 122, and the prescription request would be transmitted in the form of packetized data. Furthermore, the PPS computer 128 can be coupled to the PPS telephone 126 in place of the voice messaging system in order to guide the physician 112 through the appropriate menus for collecting information necessary to prepare the prescription. More particularly, the physician 112 may submit the audible prescription request through a microphone (not shown) attached to the physician computer 122. Other physician requests may alternatively be accommodated as well, such as email, facsimile, and wireless/mobile transmission devices including cellular telephones, pagers, and personal digital assistants (PDAs). Appropriate software can be used to convert the audible prescription request from an analog to a digital format. The digital format would thus represent a digitized prescription request. The digitized prescription request could then be segmented and transmitted to the PPS computer 128 as packetized data (i.e., data packets).

Regardless, of the manner in which the prescription request is received at the prescription processing system 110, it is converted to a digitized format (i.e., a digitized prescription request). It should be appreciated that no conversion is necessary when the PPS computer 128 receives the prescription request in a packet format. Such digitized formats include for example, ASCII, formatted text, Microsoft® Word, WordPerfect® standard facsimile formats, standard wireless transmission formats, etc. Additionally, the digitized format can optionally correspond to standard digitized audio formats such as the waveform (.wav) digital sound format supported by various operating systems. In addition, if the prescription request is received in packet format, appropriate data manipulation must be performed to reassemble the data packets and recover the original information.

According to one embodiment of the invention, an identification file can be created for the digitized prescription request. The identification file is preferably in the form of an ASCII, or text, file that stores, in part, identification data for the digitized prescription request. The identification file can include, for example, an existing prescription number and/or a member identification number. The identification file can also be used to provide quick and convenient access to prescription requests without the need to decode the digitized data.

In addition to the foregoing, the database 130 can be configured in many standard ways. For example, one exemplary database 130 configuration can include software that is running on the PPS computer 128 and storing data on a mass storage device, such as a magnetic disk drive, optical disk drive, CD-ROM, DVD, or other appropriate storage media. Alternatively, the database 130 can be part of a dedicated or stand alone system (e.g., a database system) that is operatively coupled to the PPS computer 128 and used principally for storing data, including the prescription files, while also allowing retrieval of the same data by the PPS computer 128. According to such an arrangement, appropriate hardware and software would be provided to interconnect the database system and the PPS computer 128.

While FIG. 1 illustrates the prescription processing system 110 as including various components incorporated into one, or physically located within close proximity of each other, it should be noted that the individual components need not be located in the same physical location. Rather, individual components can be located in remote locations and configured to interface and interact with each other over various communication network such as the Internet, a private network, etc. For example, a database 130 can be provided in a remote physical location while the header entry agent 132 and PPS computer 128 establish a connection over the Internet in order to store and retrieve data. Similarly, the in-house pharmacist 134 can be at a different physical location from the database 130, the header entry agent 132, etc.

According to the exemplary embodiment of the invention illustrated in FIG. 1, the header entry agent 132 accesses the digitized prescription request stored in the database 130. General information contained in the digitized prescription request is transcribed into, for example, a printable or file format or other format. The general information refers to non-medication related information such as the member's name and identification number, information regarding the physician 112 and patient 114, etc. The header entry agent 132 can also, for example, transcribe the general information to a file that can be saved on the PPS computer 128. In essence, the transcription can be in any format that can be retrieved, read, or printed.

The header entry agent 132 can access the digitized prescription request either directly through the PPS computer 128, or using a terminal operatively coupled to either the database 130 or the PPS computer 128. It should be noted that access to the digitized prescription request through the PPS computer 128 entails processing the digitized prescription file in order to decipher or parse its contents. If the prescription request is submitted via facsimile, then the header entry agent 132 preferably retrieves the general information from the facsimile printout rather than the digitized prescription request.

Furthermore, the header entry agent 132 can be in the form of a person or an intelligent software program. As an intelligent software program, the header entry agent 132 can be configured to automatically retrieve digitized prescription requests from the database 130 at regular time intervals or when a certain number of digitized prescription requests have been received and stored by the prescription processing system 110. According to an exemplary embodiment of the invention, the computerized header entry agent 132 can be in the form of a program that accesses a digitized prescription request, processes the digitized prescription request, and performs voice recognition techniques to convert part of the digital audio file to a text or other formatted data file. If a person performs the task of the header entry agent 132, then the digitized prescription request is simply processed and transcribed in a conventional manner (i.e., providing an audio output of the digitized prescription request and transcribing its content).

Once the general information has been transcribed, the digitized prescription request is forwarded to, or accessed by, an in-house pharmacist 134 associated with the prescription processing network 100. The in-house pharmacist 134 reviews the digitized prescription request and transcribes prescription-related information contained therein. Accordingly, the in-house pharmacist 134 or other individual, medical personnel and the like, that is authorized and has the necessary skills to independently write a prescription does not have to focus on reviewing the general information. The in-house pharmacist 134 uses the transcribed prescription-related information to prepare a completed prescription form that contains all the information necessary to prepare the medication (or prescription). If the prescription request is submitted via facsimile, then the in-house pharmacist 134 reviews the facsimile printout and retrieves prescription-related information in order to prepare the completed prescription form. According to one embodiment of the present invention, the in-house pharmacist 134 can listen to the digitized prescription request and double check the general information transcribed by the header entry agent 132. Such a process can improve the accuracy of prescriptions processed by the prescription processing system 110.

According to one embodiment of the invention, the completed prescription form is then transmitted or forwarded to a predetermined filling pharmacy (e.g., a local pharmacy 116) within the vicinity of the patient 114. The local pharmacy 116 can be selected based on relative location to the patient 114, preferred locations, etc. Alternatively, the filling pharmacy where the completed prescription form is transmitted, or forwarded, can be a regional pharmacy 138 associated with the prescription processing system 110. Once received at the predetermined filling pharmacy, a local pharmacist 140 fills the prescription based, in part, on information contained in the completed prescription form.

Finally, the patient 114 visits the local pharmacy 116 and retrieves the medication (e.g., the filled prescription). If a regional pharmacy 140 is used, then the filled prescription can be mailed, or otherwise delivered, to the patient 114.

The disclosed prescription processing network 100 can incorporate various techniques in order to prevent, or at least minimize, fraud. For example, if open (i.e., public) communication networks are used, various encryption/decryption techniques can be used during transmission in order to ensure security, or at least minimize possible breaches in security. In addition, security protocols such as the SSL protocol found in most conventional web browsers can be used. Various other methodologies such as security tokens and/or secure portals can also be used. The present invention can also be configured to provide internal safeguards for protecting data and privacy. For example, the database 130 can be configured such that it stores unique information regarding, for example, the physician 112 or medical establishment. Such information can include unique passwords, telephone numbers, etc. The information would be collected as part of an initial (or application) phase before prescription requests will be accepted. When a new prescription request is received by the prescription processing system 110, the physician 112 (or user) would be prompted to submit his or her password, telephone number, etc. Alternatively, the physician 112 can use his or her assigned DEA number for identification/security purposes instead of a password or the like. Either or all of these identification/security numbers and/or passwords can be used to define predetermined relationships, or criteria, for verifying the physician's identity.

Furthermore, appropriate hardware and software can be integrated into the PPS telephone 126 in order to capture the telephone number e.g. ANI—automatic number identification and/or DNI—destination number identification from an incoming call (e.g., similar to current "caller ID" features) and associate it with the prescription request. When the header entry agent 132 transcribes the general information, the password, telephone number, etc. submitted by the physician 112 are compared to what is currently stored on the database 130 in order to identify a predetermined relationship. The predetermined relationship can correspond, for example, to a match between the information submitted by the physician and the information stored on the database 130. According to an optional feature, the ANI can be used to automatically identify the caller's location and/or calling number. The predetermined relationship would then correspond to a match between the caller's location and/or calling number and the information (e.g., calling or telephone number) stored on the database 130. If there is a discrepancy or the predetermined relationship is not satisfied, then the header entry agent 132 would contact the physician's office to indicate the problem and determine if someone was fraudulently trying to submit the prescription request. Such header information may optionally be encrypted as well.

Security precautions can also be taken if the prescription requests are submitted via facsimile. According to one embodiment of the present invention, prior to submitting the prescription request, the physician 112 must contact the prescription processing system 110 and indicate that he or she would like to submit a prescription request. Next, the physician 112 must submit his or her facsimile number. The prescription processing system 110 then establishes as a separate connection to the physician's facsimile machine and transmits a prescription request form that includes a facsimile number for the prescription processing system 110. The physician 112 supplies all the necessary information required by the prescription request form including, at least, information required to fill the prescription. The completed prescription request form would then be transmitted back to the prescription processing system 110 via facsimile.

According to one embodiment of the invention, the prescription processing network 100 can be configured for mail order processing. According to such an embodiment the in-house pharmacist 134 transcribes prescription related information and prepares a prescription form. The prescription form can then be filled by the in-house pharmacist 134 and mailed to the patient 114. Alternatively, the prescription form can be transmitted to a central or regional pharmacy 138 (or other location) of with the prescription processing network 100. One or more local pharmacists 140 would be available to fill received prescription forms. The filled prescriptions would then be mailed to patients 114 from the central or regional pharmacy 138.

Processing Prescription Requests

Figure 2:
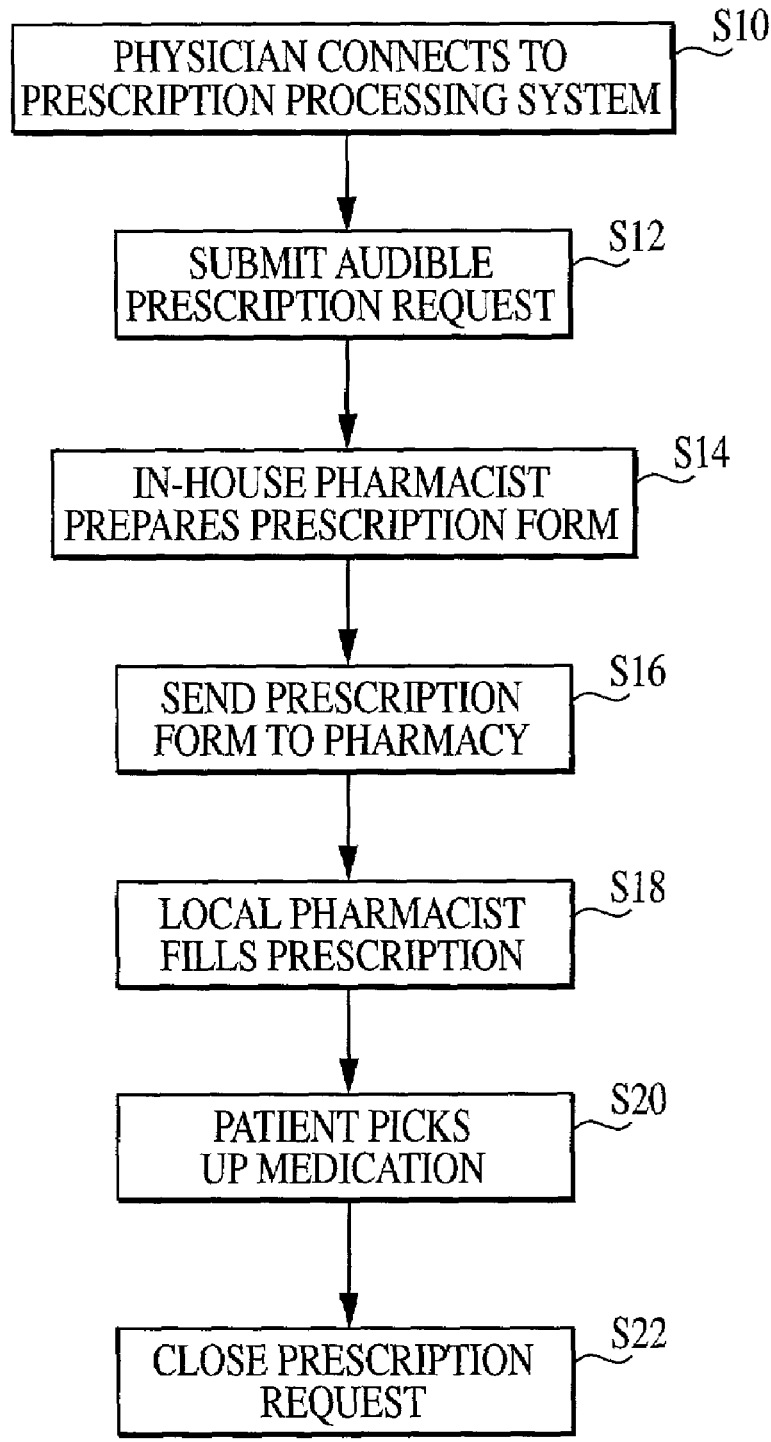
FIG. 2 is a flow diagram generally illustrating how prescription requests are processed.

FIG. 2 is a flow diagram that generally illustrates the methodology for processing prescription requests according to an exemplary embodiment of the present invention. The process begins at step S10, where the physician or other medical personnel/clinician connects to the prescription processing system. As previously indicated, this can be accomplished using, for example, a telephone connection or a computer connection. The physician submits an audible prescription request at step S12. The in-house pharmacist, or other medical personnel (including a medical doctor) capable of independently writing a prescription, prepares a prescription form based, at least partially, on the audible prescription request or other request that can be securely transmitted by the physician but possibly requiring independent review/verification at step S14. The prescription form is then sent to the filling pharmacy or optionally other location capable of independently writing a prescription and at step S16. It should be noted that the pharmacy discussed at step S16 can also be the local, regional, or central pharmacy discussed above. At step S18, the local pharmacist reviews the received prescription form, independently verifies it, and fills the prescription. At step S20, the patient visits the filling pharmacy in order to retrieve the filled prescription. Alternatively, if a central or regional pharmacy is used, then the filled prescription is mailed or otherwise delivered to the patient after performing step S18. At step S22, the prescription request is closed.

It should be noted, that step S22 is not mandatory for operation of the prescription processing network. In other word, there is no need to close the prescription request. Furthermore, where the prescription request is optionally closed, such a step need not be performed after the patient picks up the medication. Rather, such a step can be performed, for example, once the prescription form has been sent to the filling pharmacy. Alternatively, such a step can be performed once the filling pharmacy has confirmed receipt of the prescription form. As can be seen from the above examples, various alternatives exist for specifically implementing step S22.

Figure 3:
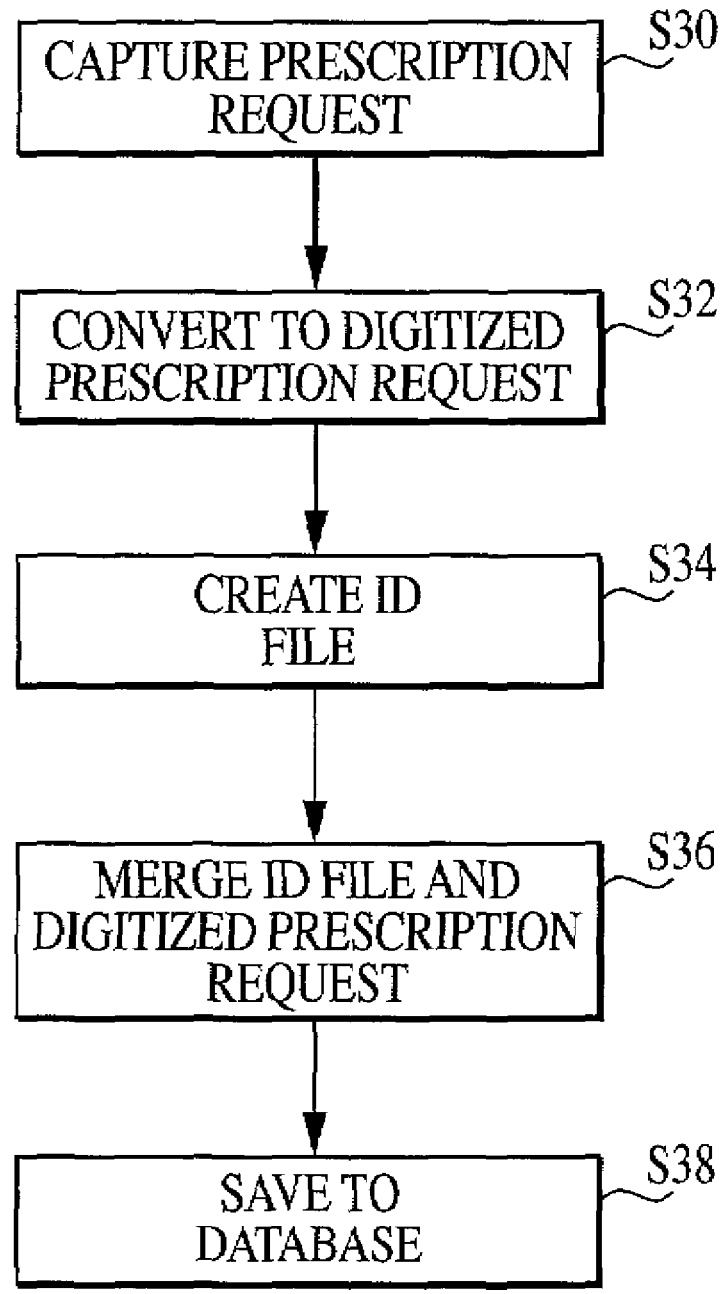
FIG. 3 is a flow diagram generally illustrating the steps performed by the prescription processing system.

FIG. 3 is a flow diagram which illustrates the steps performed by the prescription processing system after a connection has been established with the physician. At step S30 the prescription request submitted by the physician is captured by the prescription processing system. The prescription request can be captured using various well known formats, or systems, for recording information from a telephone or other appropriate communication source or other communication data from the physician or medical personnel. The captured prescription request is converted to a digitized prescription requestor other suitable digital representation as appropriate/needed at step S32. In the event the data communicated is already in digital format, no conversion is necessary. As previously indicated, the digitized prescription request represents an analog to digital conversion of the audible prescription request submitted by the physician. At step S34, an identification file or other standard way of creating or attaching an identification is created for the digitized prescription request. The identification file contains, in part, identification data associated with the prescription such as an existing prescription number or a member ID.

According to one embodiment of the present invention, once the member ID is received, the prescription processing system can retrieve formulary and/or prescription coverage information for the member. The formulary information identifies particular medications and terms for insurance coverage. The formulary information can be optionally used to dictate the medication choices available to the physician when submitting a prescription request. For example, a physician may not be able to request a particular brand name drug. Instead a generic version would have to be prescribed. In other situations, the formulary can indicate that a particular drug is not acceptable to treat an illness. The physician would then prescribe an acceptable substitute to treat the illness.

At step S36, the identification file or data is merged with the digitized or other prescription request. According to one embodiment of the present invention, the two files are concatenated and stored as part of an archived file. Alternatively, the identification file and the digitized prescription request can be assigned the same name, but with different extensions that identify the particular file type, in order to display the common relationship. At step S38, the concatenated files, or individual files for the prescription request, are saved to the database.

Figure 4:
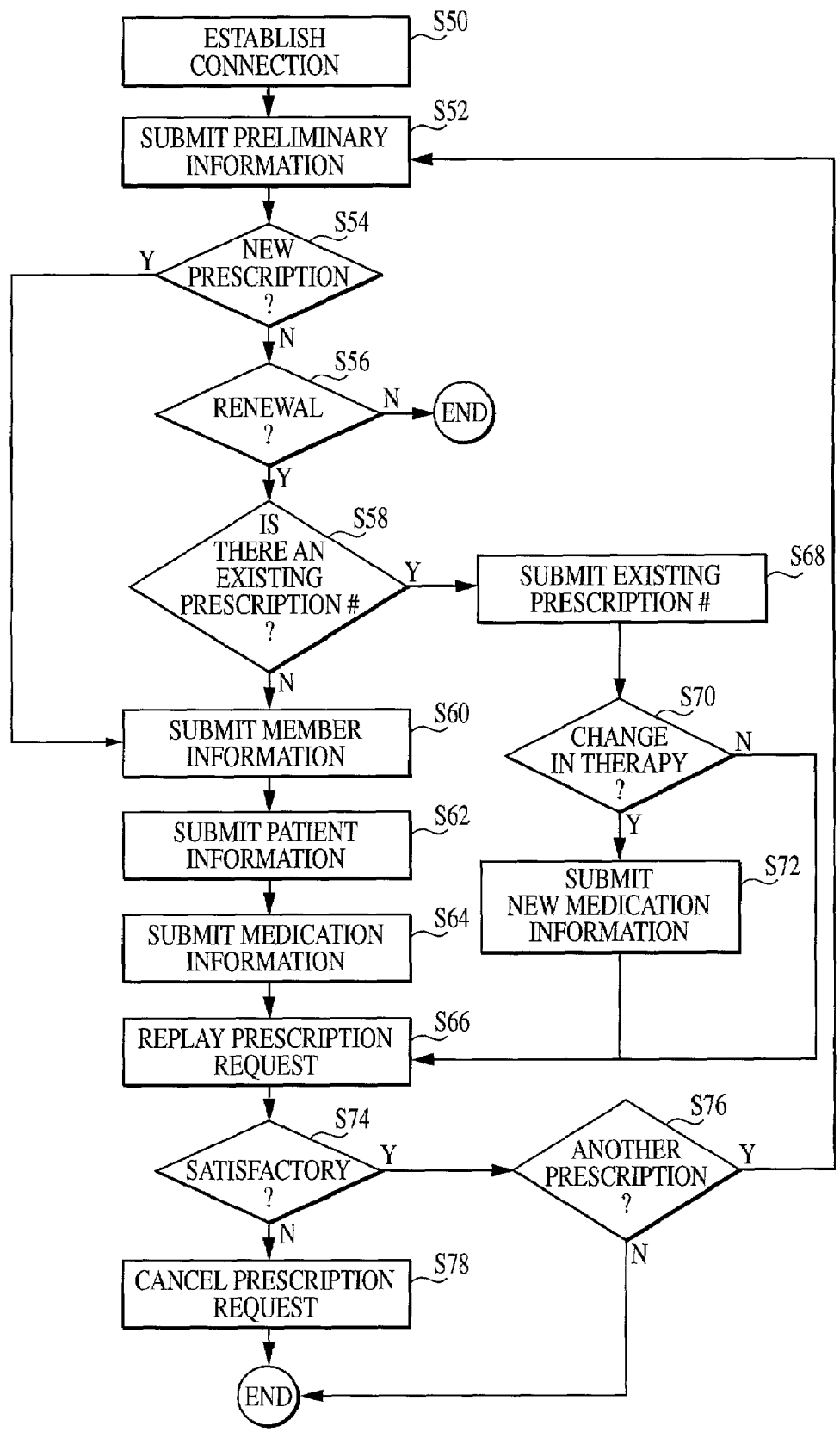
FIG. 4 is a flow chart detailing the steps performed when processing prescription requests.
Figure 5A:
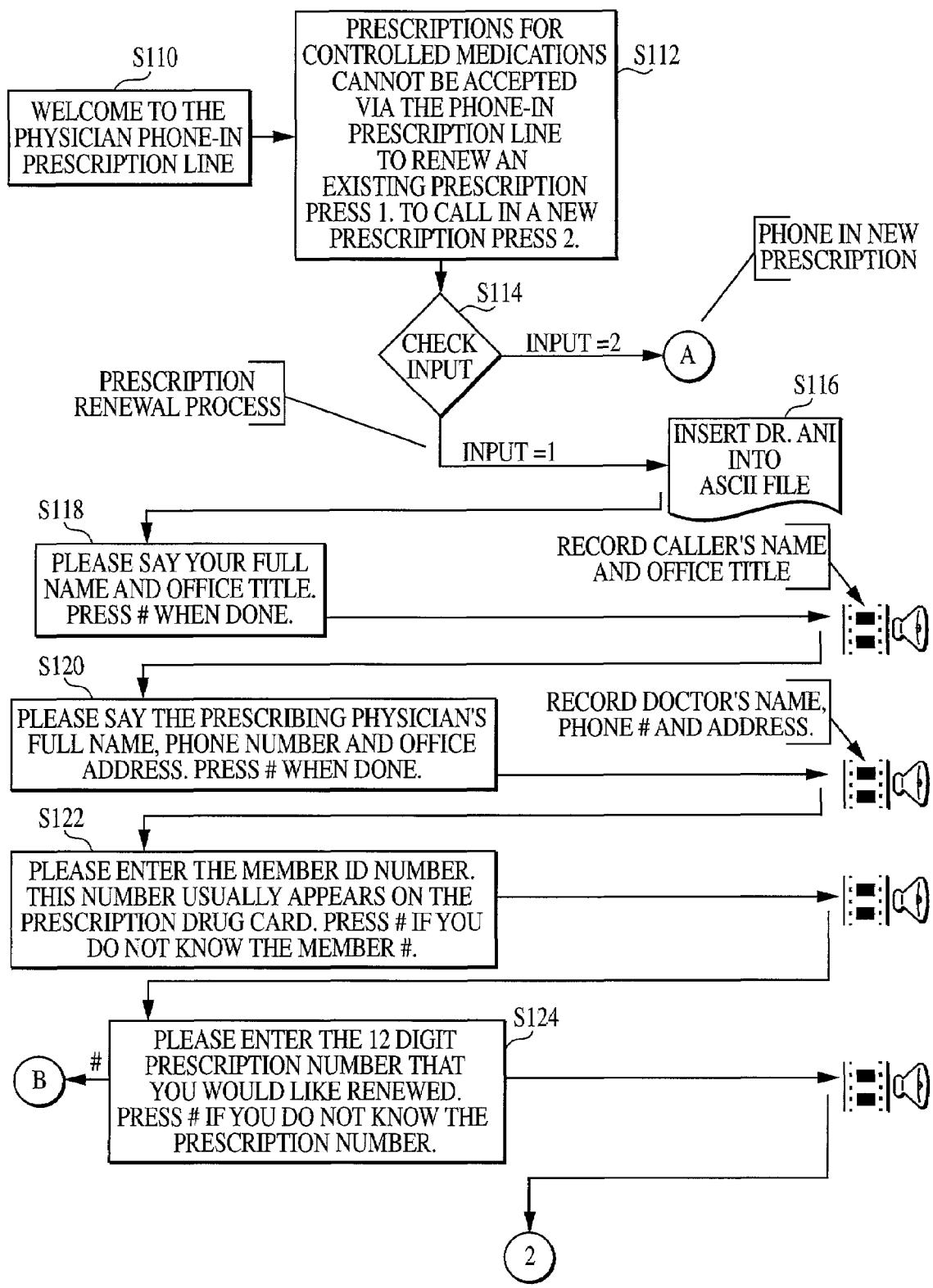
FIGS. 5A–5E are a flow diagram illustrating how prescription requests are processed according to an exemplary embodiment of the present invention.
Figure 5B:
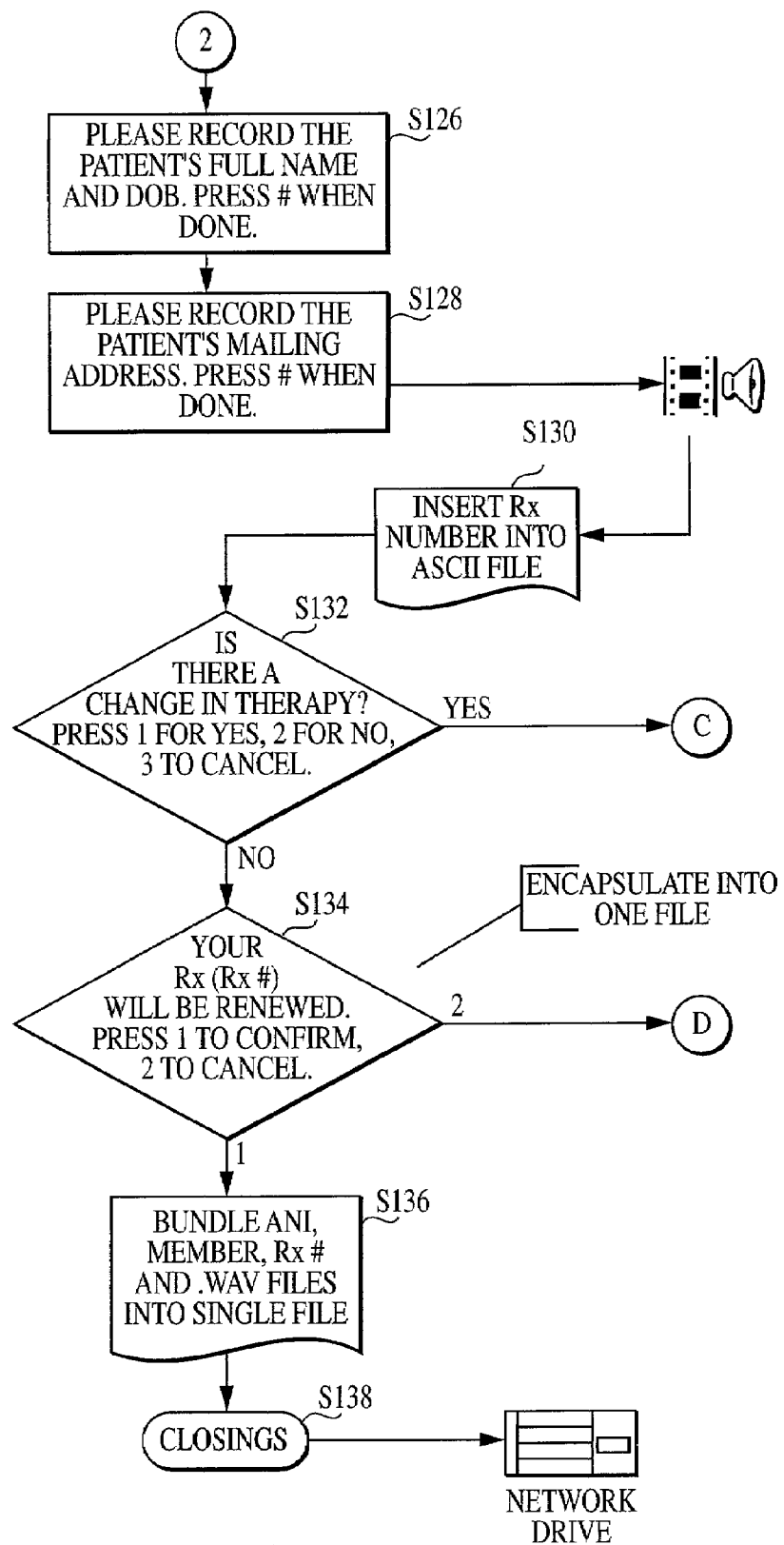
Figure 5C:
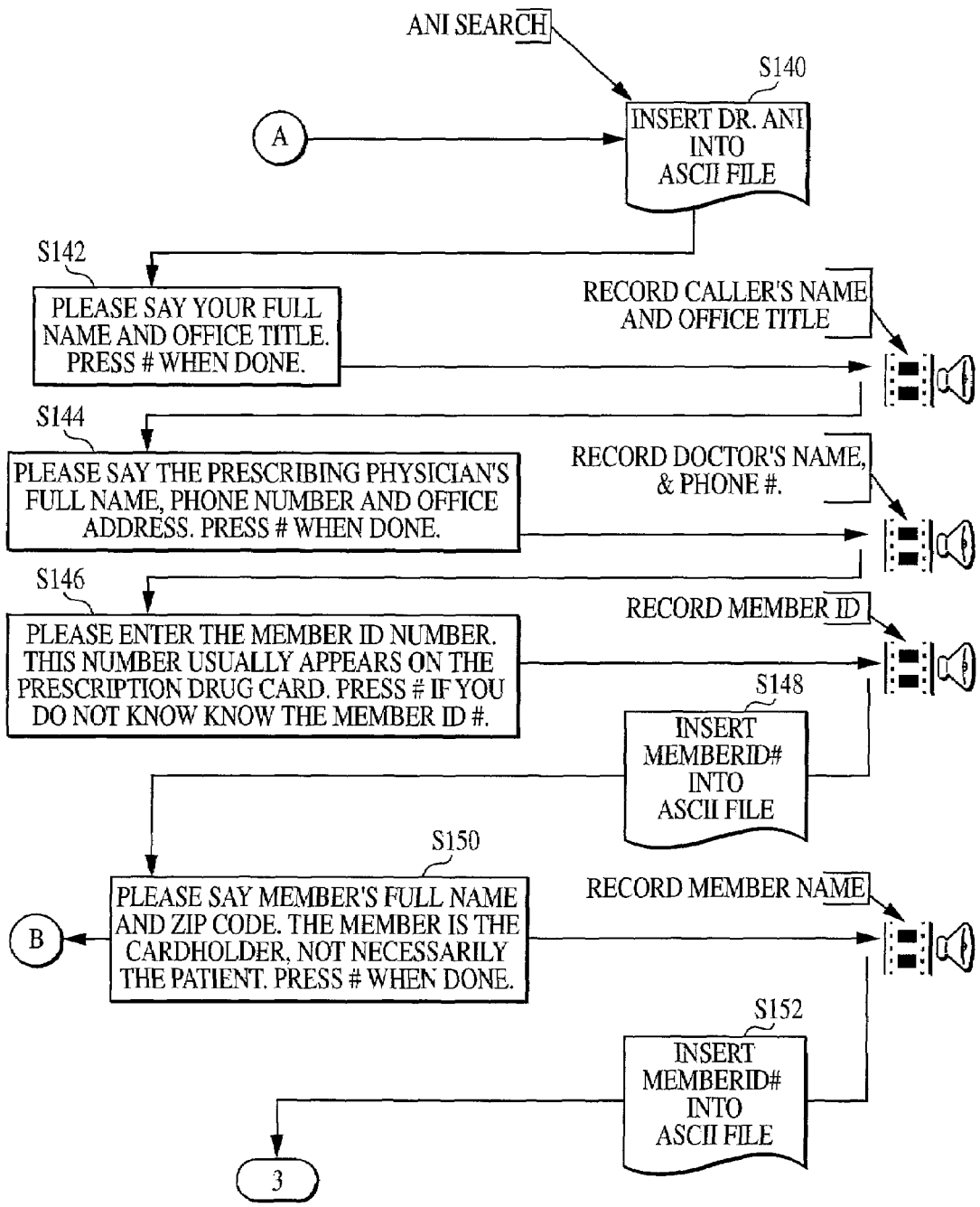
Figure 5D:
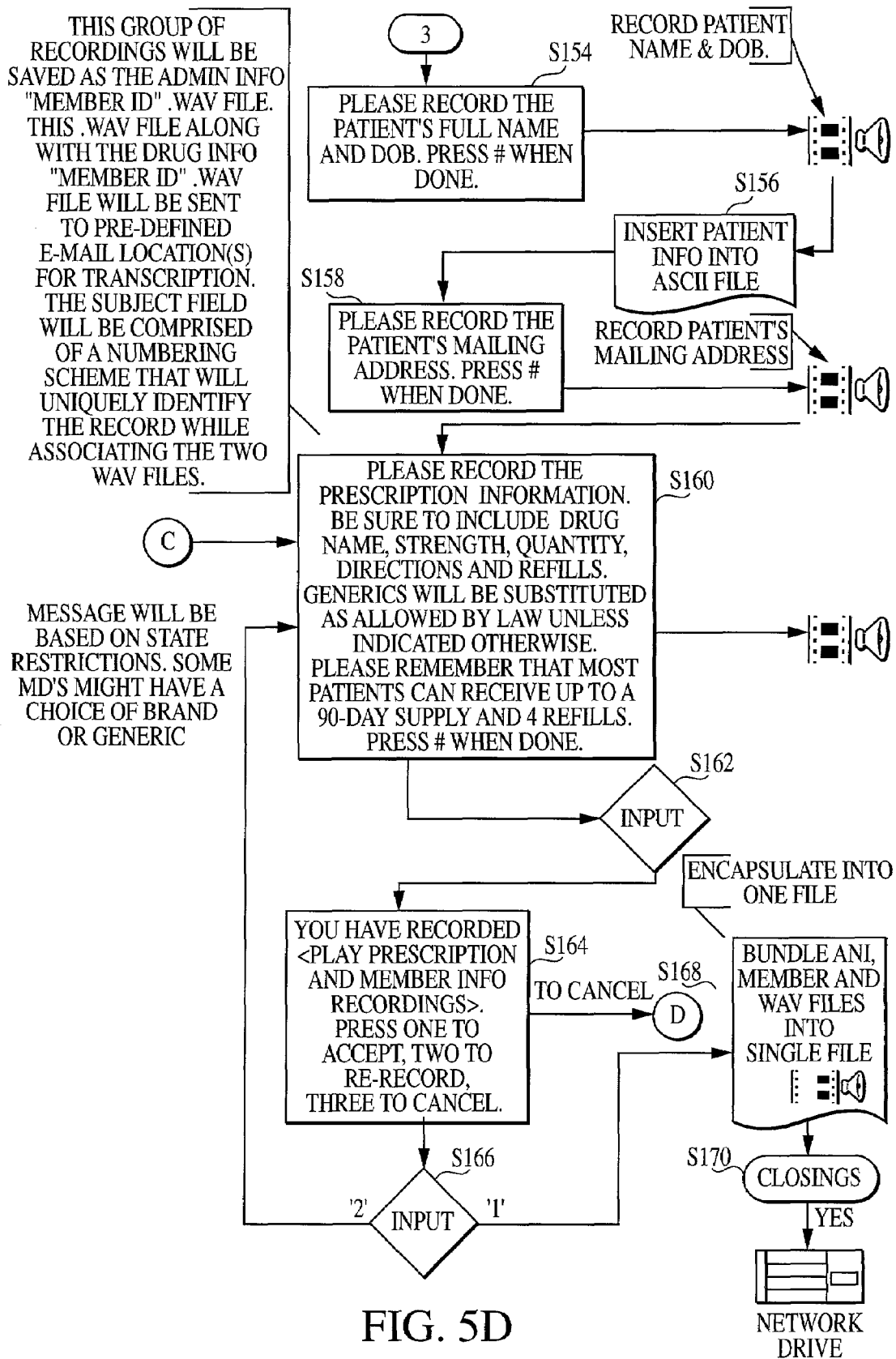
Figure 5E:
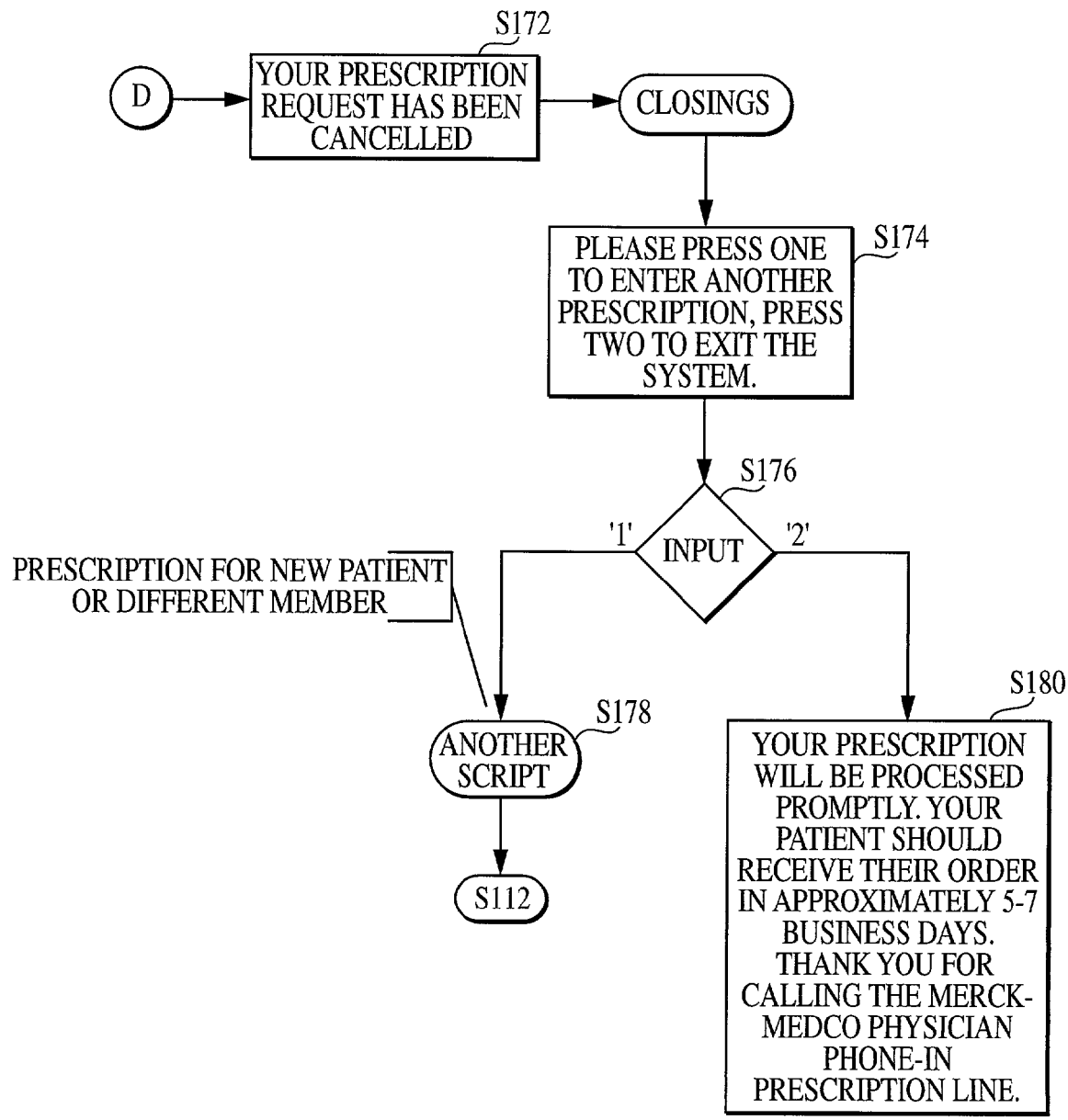
Figure 6A:
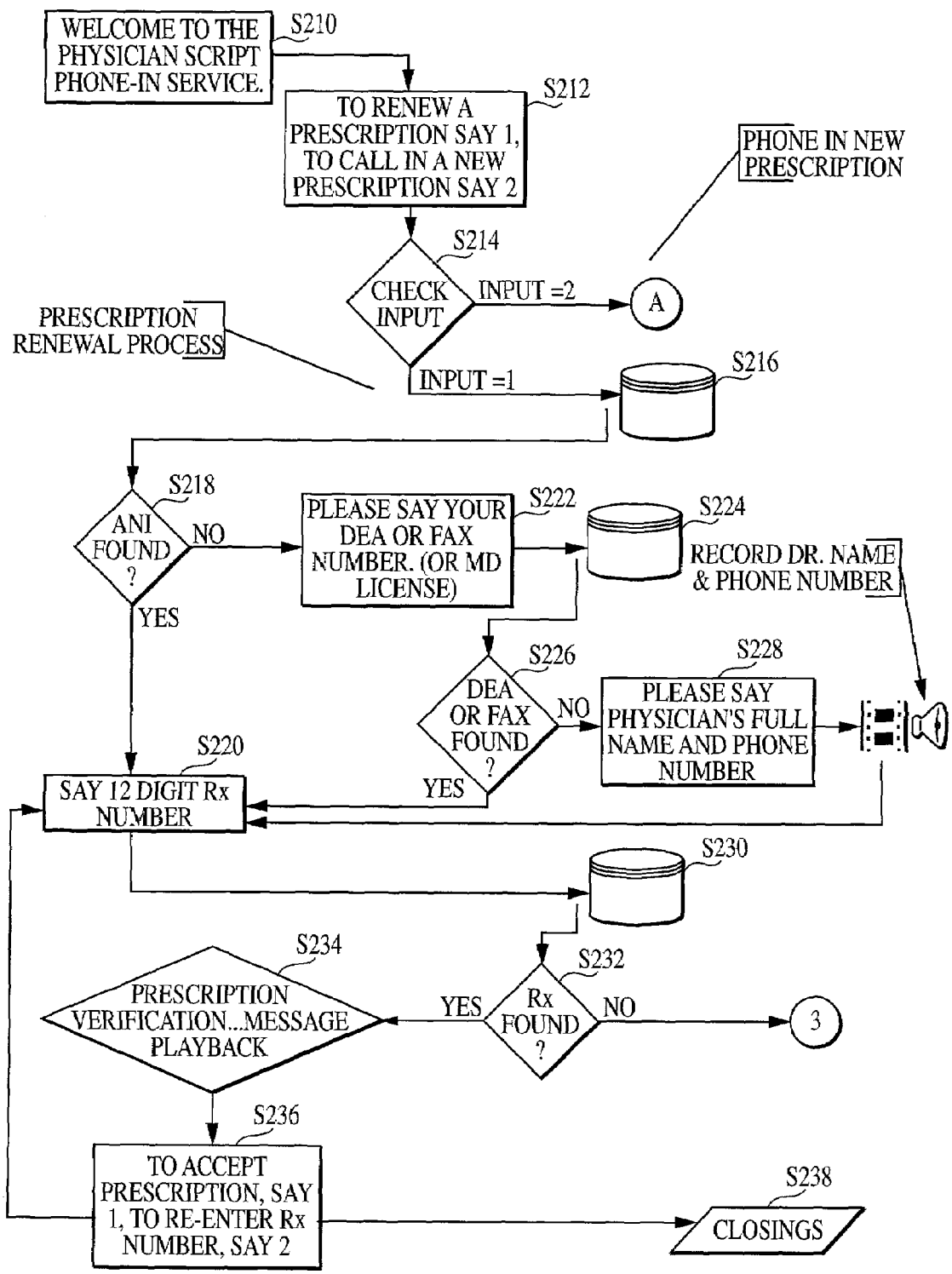
FIGS. 6A–6D are a flow diagram illustrating an alternative implementation of the prescription processing system of the present invention.
Figure 6B:
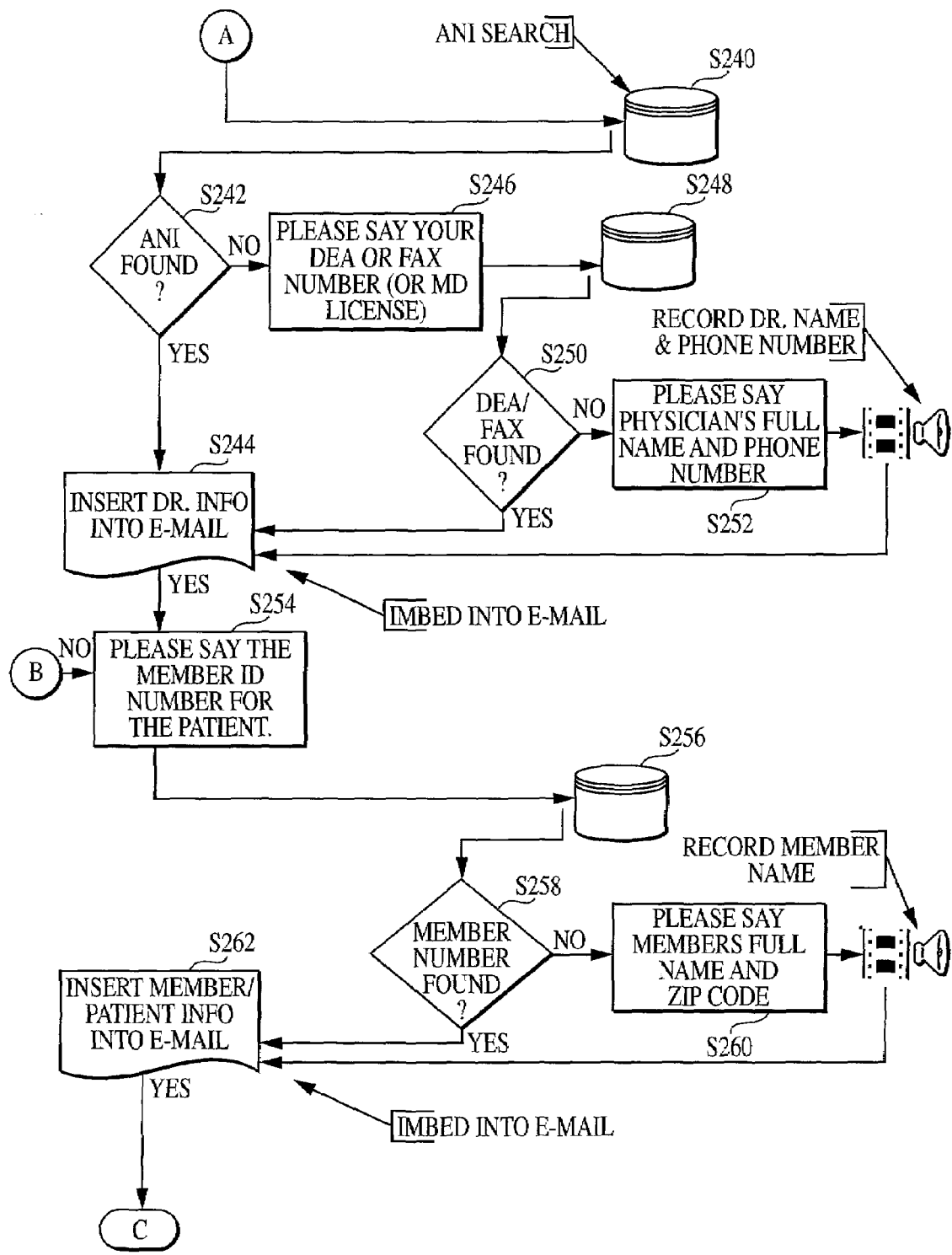
Figure 6C:
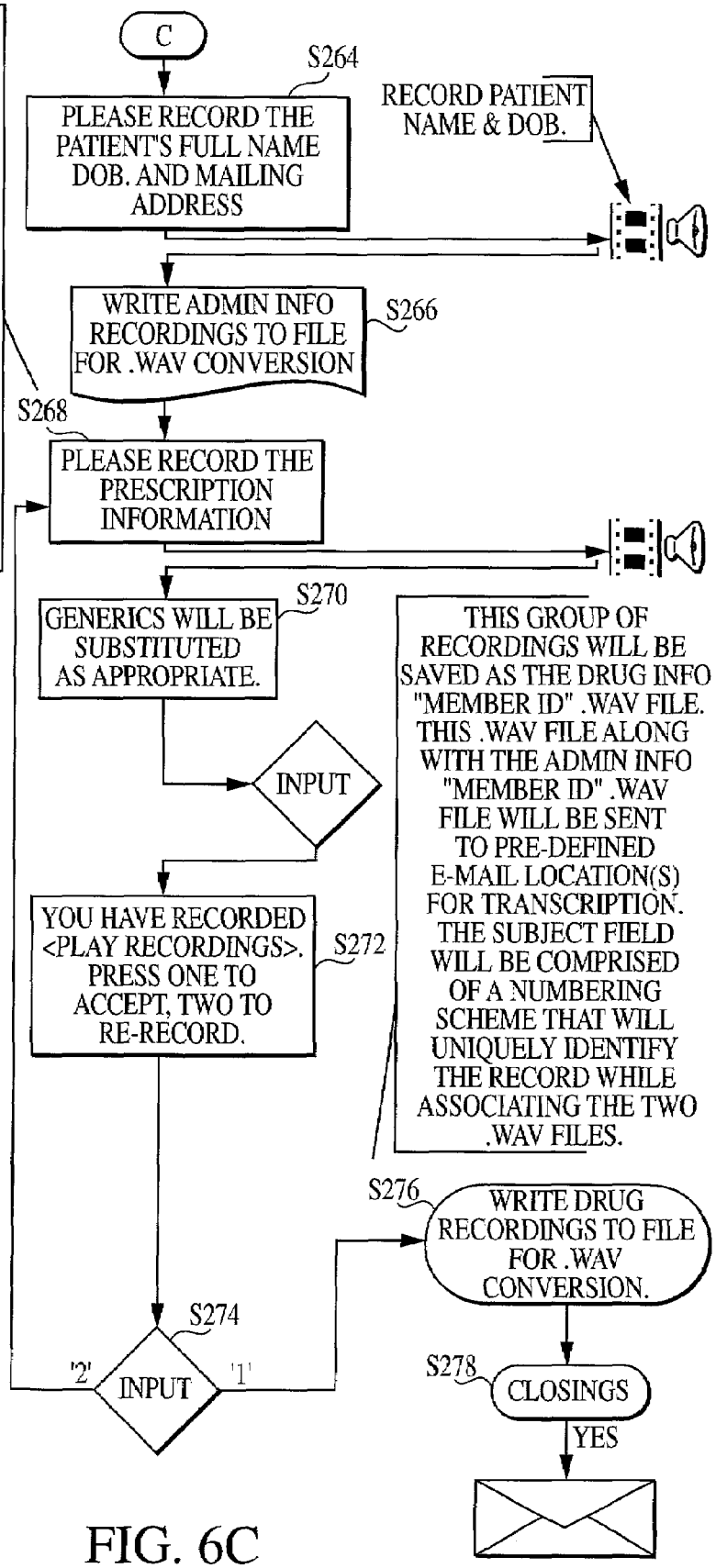
Figure 6D:
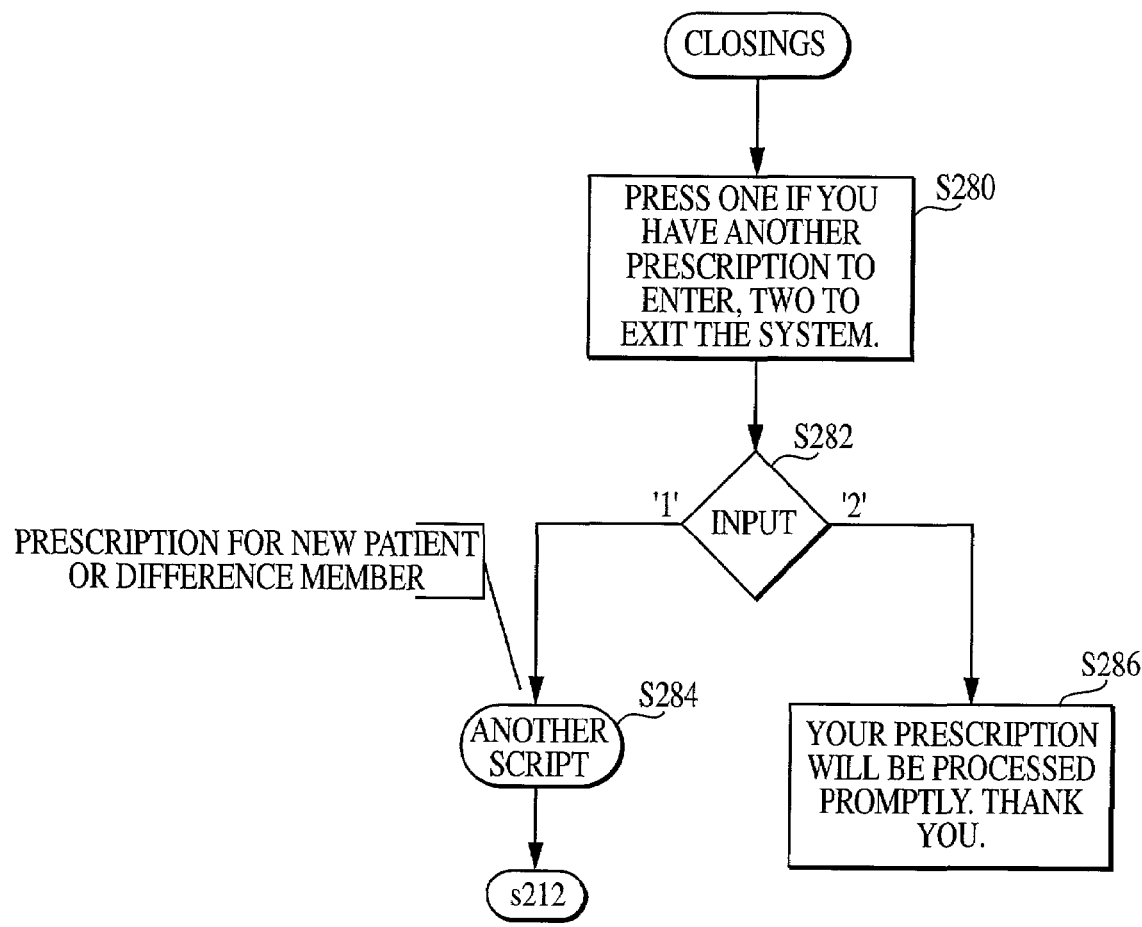
Figure 7A:
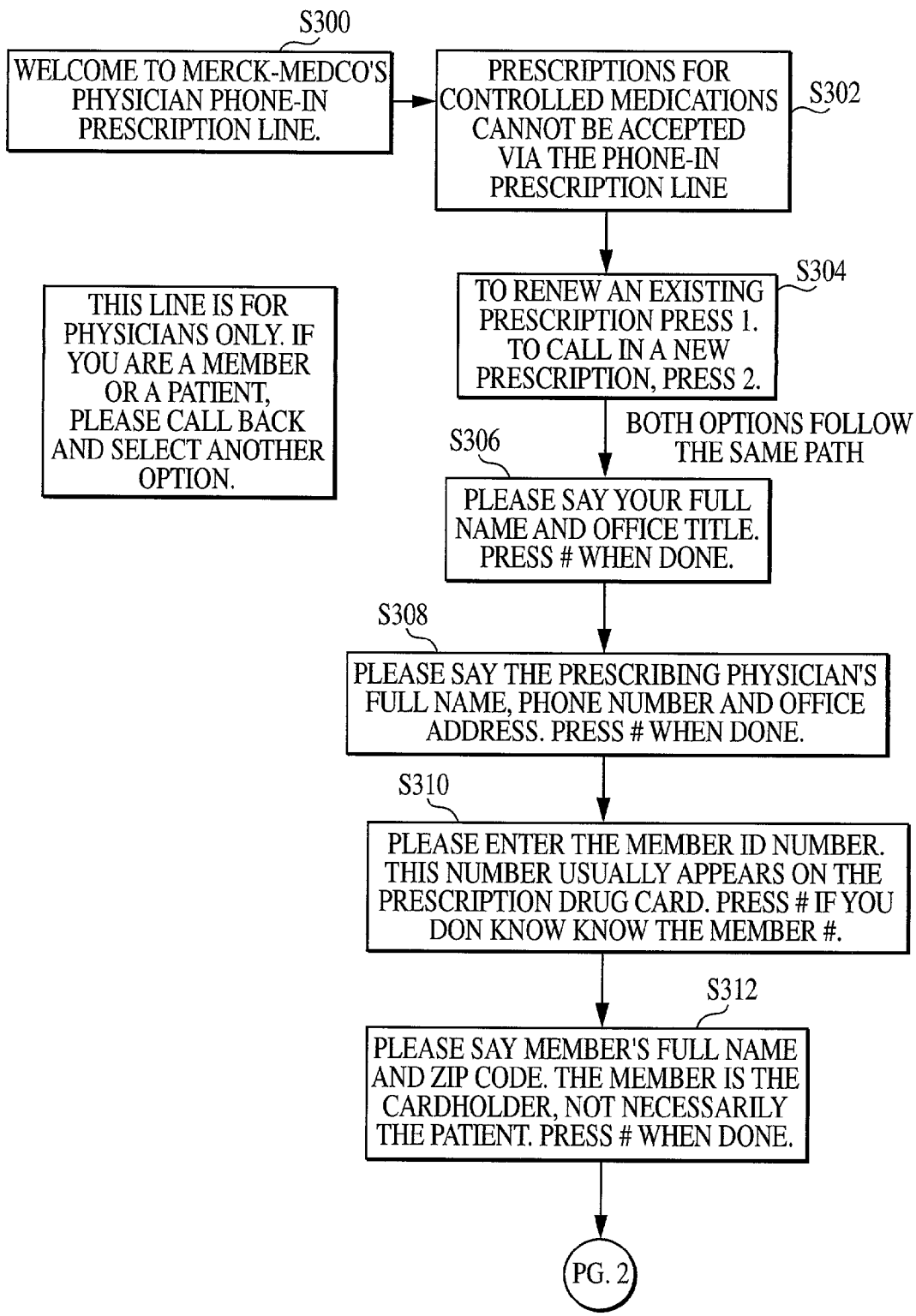
FIGS. 7A–7C are a flow diagram illustrating an another implementation of the prescription processing system of the present invention.
Figure 7B:
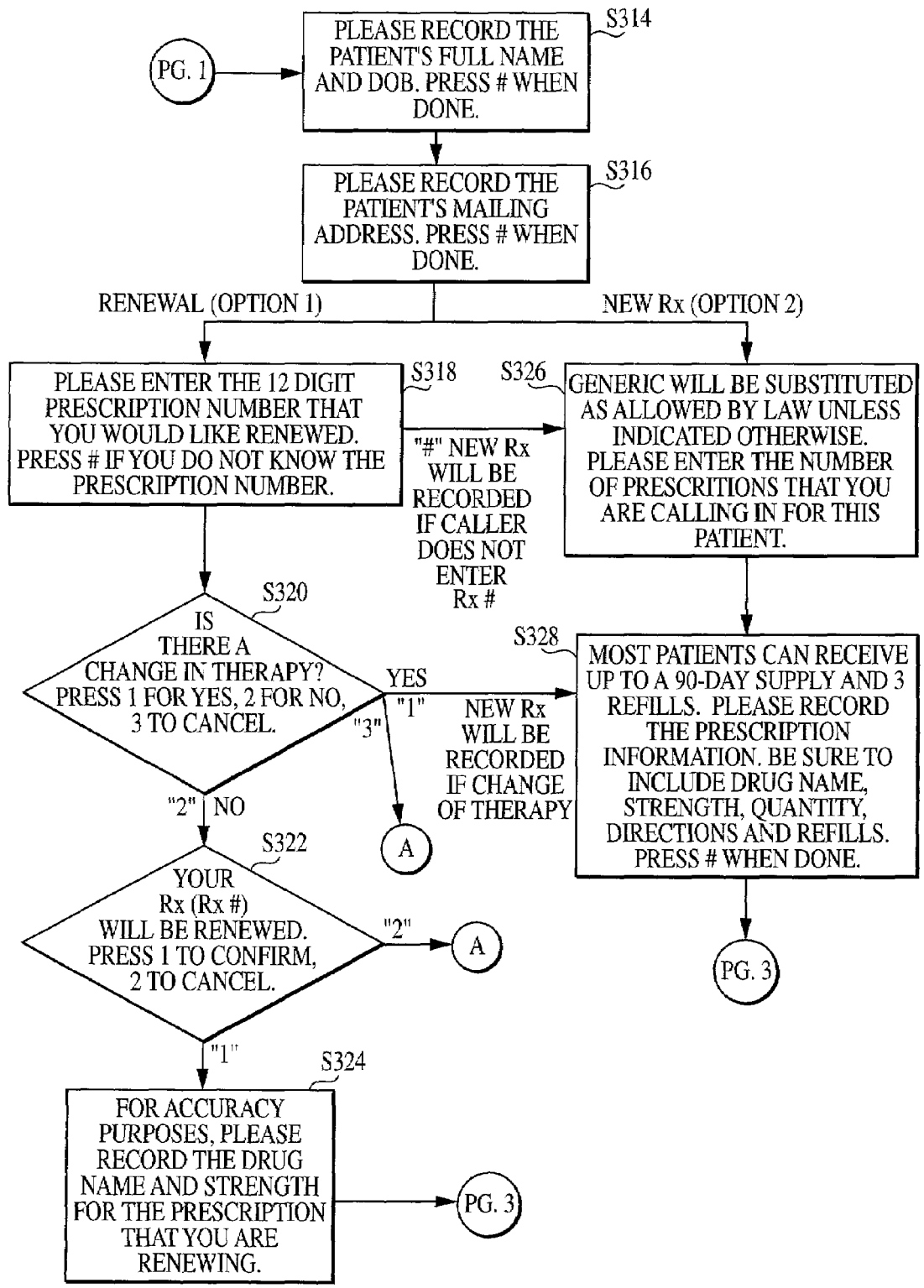
Figure 7C:
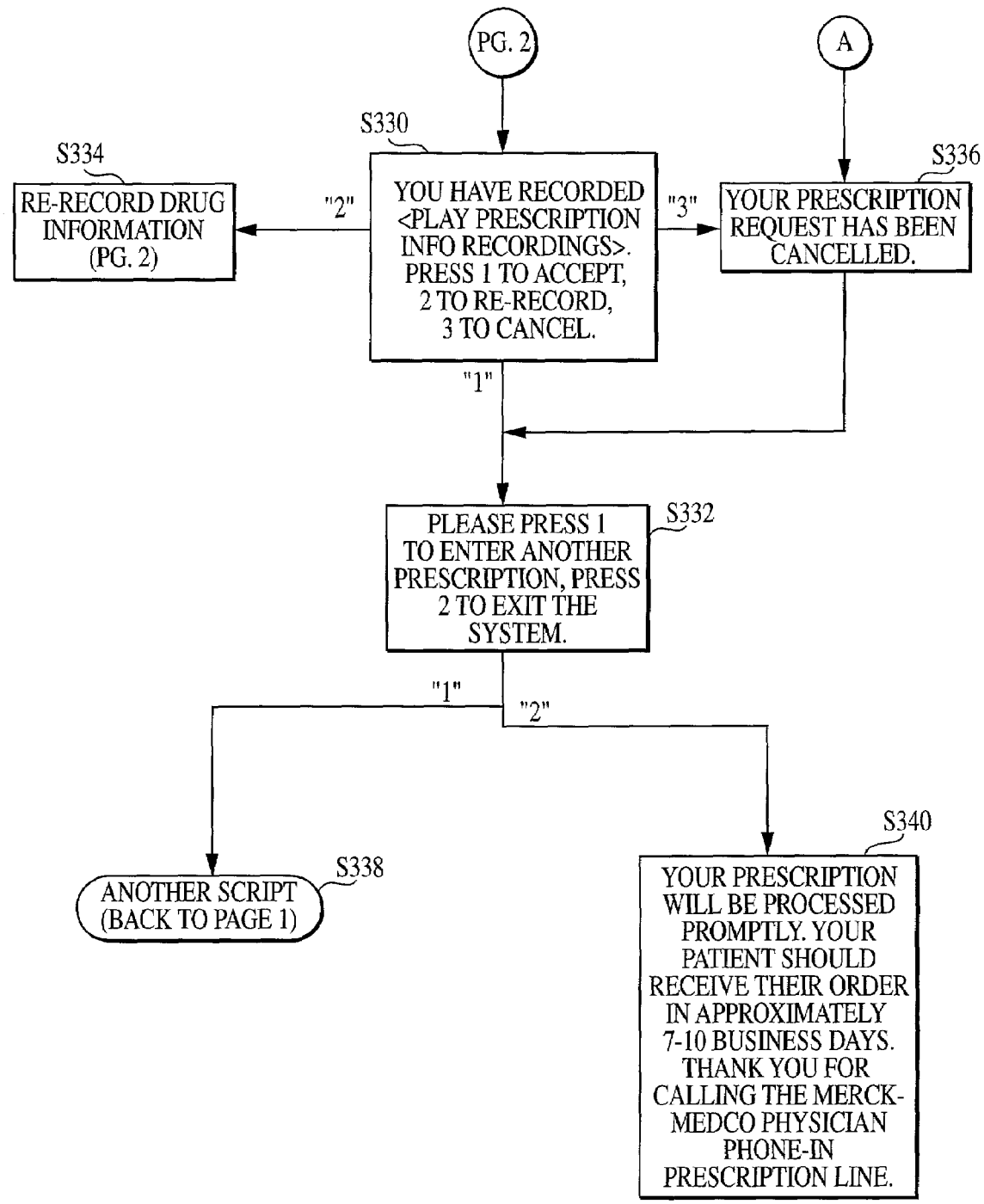

FIG. 4 is a flow chart which details the steps performed while processing prescription requests. At step S50, a connection is established to the prescription processing system. As previously stated, the physician or medical personnel, nurse, and the like, will typically be the person establishing the connection, although other qualified or licensed medical personnel or administrators can establish the connection and submit information for the physician. The connection can also be established in a variety of ways. According to one embodiment of the present invention, the connection is established over a conventional telephone line. Other embodiments, for example, can allow connection using a computer system, with or without a conventional telephone connection. It should be noted that various other connection types, including optical, wireless, or satellite can also be used.

At step S52, preliminary, or general, information is submitted. The preliminary information is used to identify, for example, the subscriber (e.g., physician or other medical personnel) and/or insurance information. According to an exemplary embodiment of the invention, the subscriber information can be used to identify a physician office, hospital, etc. For example, the subscriber information can include the physician's name, office address, and office telephone number. The insurance information pertains to the particular insurance carrier providing coverage for the prescription costs, and can be obtained from the member's identification card. In addition, information regarding the user can also be requested. The user information can include, for example, the name of the person submitting the prescription request and his or her affiliation with the physician or medical establishment. If the physician is submitting the prescription request, then it may not be necessary to further submit user information.

At step S54, it is determined whether the prescription request is for an entirely new prescription. If the prescription request is for a new prescription, then control passes to step S60. If the prescription request is not for a new prescription, then control passes to step S56. At step S56, it is determined whether the prescription request is for a renewal (i.e., renewing an existing prescription). If the prescription request is not for a renewal, then the process ends. If the prescription request is for a renewal, then at step S58 it is determined whether there is an existing prescription number. The prescription number can refer to, for example, the twelve digit identification number printed on the prescription form. If there is no existing prescription number, then control passes to step S60 where member information must be submitted. Typically, the member ID number printed on the insurance card is sufficient for satisfying this query. According to an exemplary embodiment of the present invention, if there is no member ID number on the insurance card, then at step S60, the member's name and address is submitted.

At step S62, information regarding the patient who will be taking the medication is submitted. The patient information can include, for example, the patient's name, address, date of birth, sex, existing medical conditions, etc. In addition, the patient information can include existing medication being taken by the patient, thereby avoiding adverse interactions between different medications.

At step S64 information regarding the medication is submitted. The medication information can include, for example, the name of the medication, the strength of the medication, and the dosage that should be taken by the patient. Furthermore, the medication information can include an indication as to whether or not generic versions of the medication can be used, or if brand name medication must be used. Depending on the specific implementation of the invention, additional information regarding the prescription can be submitted. More particularly, the prescription information is not limited to the information described above. Rather, any information relating to the prescription and/or medication can be submitted. At step S66, the prescription request is replayed, displayed, or transmitted to or for the user in order to obtain confirmation that all the information was accurately submitted.

Returning again to step S58, if there is an existing prescription number, the system prompts the user to submit the existing prescription number. At step S70 it is determined whether there is a change in therapy for the patient. If there is a change in therapy, then new medication information regarding the prescribed medication and/or dosage is submitted at step S22. The new medication information refers to the specific changes that the physician determines necessary for treating the patient. Once the new medication information has been submitted the prescription request is again replayed or displayed. If there is no change in therapy, however, control passes to step S66 where the prescription request is replayed. At step S74, it is determined whether the prescription request contains all of the information desired by the physician or user. If all the information is correct and satisfactory, then control passes to step S76.

At step S76, the user is prompted to indicate whether he or she would like to submit another prescription request. If another prescription request will be submitted, then control returns to step S52. If it is determined at step S74 that the prescription request is inaccurate or unsatisfactory, then control passes to step S78 where the prescription request is cancelled. The process subsequently ends. Additionally, if the user will not submit an additional prescription request at step S76, then the process also ends.

FIGS. 5A–5E are flow diagrams illustrating how prescription requests are processed according to an exemplary embodiment of the present invention. The process begins at step S110 where the caller, physician, or appropriate personnel, establishes a connection with the prescription processing system. Once the connection is established, the caller is greeted with a message identifying the prescription processing system. At step S112, an optional message indicating that prescriptions for controlled medications cannot be accepted via the prescription processing system is played for the physician.

Next, the caller is asked whether he or she is renewing an existing prescription or requesting a new prescription. If the caller is renewing a prescription, he or she can select this option by either saying the word "1", or pressing the "1" key on the telephone keypad. To submit a new prescription, the caller can either say the word "2" or press the number "2" on the telephone keypad. At step S114, the prescription processing system examines the physician's input. If a new prescription is being submitted, then control passes to block A. Alternatively, if a request to renew a prescription is being submitted, then the caller is prompted to submit his or her origination or calling number. Alternatively, if the appropriate standard equipment is available, automatic number identification (ANI) can be automatically provided for the calling number. If an authorized personnel other than the physician is placing the call, then he or she must provide the physician's telephone number. Again, the number can be submitted either verbally, or through the use of the numeric keypad on the telephone. Once submitted, the telephone number is inserted into an ASCII file.

At step S118, the caller is prompted to say his or her full name and optionally official title. Preferably, the pound (#) key can be pressed to provide an indication that the caller has finished saying the requested information. Alternatively, it should be noted that the prescription processing system can be configured to detect when the caller has completed saying the information based on a predetermined period of vocal inactivity. As the caller is saying the requested information, the prescription processing system automatically records the information. At step S120, the caller is prompted to say the prescribing physician's full name, telephone number, and office address. At step S122, the caller is prompted to enter the member ID number. As previously indicated, the member ID number generally corresponds to the identification number assigned to the member by the insurance provider. The caller is also given an option to bypass this step if he or she does not know the member ID number.

At step S124, the caller is prompted to enter the 12 digit number of the prescription that is to be renewed. If the caller is unaware of the prescription number, then control passes to block B. Otherwise, the prescription number is recorded and the process continues onto block 2. At step S126, the caller says the full name and date of birth of the patient. At step S128, the caller says the patient's mailing address. After the patient's name, date of birth, and mailing address have been submitted and recorded, the prescription number is entered into the ASCII file at step S130. At step S132, the caller is prompted to indicate whether or not there will be a change in therapy for the prescription being renewed. If there is a change in therapy, the caller can either say the word yes or press the "1" key on the telephone pad. If, on the other hand, there is no change in therapy, then the caller can say the word "no" or press the "2" key on the telephone pad. A change in therapy transfers control to block C, while no change in therapy allows the process to continue to step S134.

At step S134, the caller is informed that the prescription will be renewed. Furthermore, the prescription processing system will replay the prescription number for the caller in order to obtain confirmation that the proper prescription will be renewed. The caller must still provide an input that is indicative of whether or not he or she would like to confirm renewal of the prescription, or cancel the current prescription renewal. If the transaction is to be cancelled, then control passes to block D. Otherwise, if the prescription will be renewed, then control passes to step S136. At step S136, the physician ANI number, the member information, the prescription information, and all of the recorded inputs are bundled into a single file. As previously stated, all of the information submitted by the caller is digitally recorded and stored as a data file. Furthermore, various formatting conventions can be used in creating the digital audio files. The information can be then bundled using, for example, and archiving software that merges all of the different files into a single archive. Once the bundled file has been created, the caller is directed to the closings process at step S138. Furthermore, after directing the caller to the closings process, the information obtained by the prescription processing system is stored on a network drive, or database, where it can be subsequently accessed by the prescription processing system and various personnel.

Returning to step S114, if the caller had elected to submit a new prescription, control would have passed to block A. At this point, step S140 is performed. The caller is asked to submit (e.g., say) the physician's telephone number, and the telephone number is inputted to an ASCII file or other manner of transmitting information specifically created for the current prescription request. At step S142, the caller is prompted to say his or her full name and office title. At step S144, the caller says the prescribing physician's full name, phone number, and office number. At step S146, the caller is asked to enter the member's ID number. This can be done either audibly, or using the telephone keypad. If the caller is unaware of the member's ID number, this particular step can be bypassed by pressing the pound (#) key. If the caller does not know the member's ID number, subsequent information can be collected to later determine the member's ID by cross-referencing various information stored on the prescription processing system database. If the member's ID number is known and submitted by the caller, the information is inserted into the ASCII file for the current prescription request.

At step S150, the caller is prompted to say the member's full name and zip code. Step S150 is also performed if at step S124, the caller did not know the number of the prescription being renewed. At step S152, the member's ID number is inserted into the ASCII file. As previously indicated, the member's ID number can be determined by the prescription processing system if it is unknown to the caller. This can be accomplished, for example, by cross-referencing the member's name and zip code with existing information stored on the prescription processing system database in order to determine the member's ID number and subsequently insert the ID number into the ASCII file.

At step S154, the caller is prompted to say the patient's full name and date of birth. This information helps, in part, to determine the appropriateness and/or dosage of certain medication based on the patient's age. At step S156, the patient's information is stored in the ASCII file. At step S158, the caller is prompted to say the patient's mailing address. At step S160, the caller is prompted to say the prescription information. As previously stated, the prescription information can include, for example, the type of medication, dosage, etc. During the prescription renewal process, if there was a change in therapy, control would also have passed to step S160. At step S160, the caller submits information such as the medication name, the strength, the quantity, the dosage instructions, and refill instructions. In addition, the caller is informed that generics will normally be substituted unless otherwise indicated. Furthermore, the caller is informed that the medication can be prescribed for a period of up to 90 days, with four subsequent refills. It should be noted, however, that various other messages may be provided to the caller depending on regulations established by the federal or local authorities.

At step S162, the information provided by the caller is recorded. At step S164, the prescription processing system replays or displays the recorded information in order to obtain approval from the caller. The caller can accept the recorded prescription information by saying the word "1" or pressing the "1" key on the telephone keypad. The caller can elect to re-record the prescription information by saying the word "2" or pressing the "2" key on the telephone keypad. Finally, the caller can cancel the transaction by saying the word "3" or pressing the "3" key on the telephone keypad. If the caller elects to cancel the transaction, control passes to block D. At step S166, the caller's selection is examined. If the caller would like to resubmit the prescription information, then control returns to step S160. If the caller would like to accept the recorded prescription information, then control passes to step S168 where the physician ANI number, the member's information, and the audio or data files are bundled into a single file or other manner.

At step S170, the caller is transferred to the closings section and the bundled information is saved to the appropriate prescription processing system database. If the caller decided to cancel the prescription request at any point, he or she is provided with a confirmation message at step S172 that the prescription request has been cancelled. Regardless of whether or not the prescription request has been cancelled, the caller is still directed to the closings section. At step S174, the caller is asked if he or she would like to enter another prescription request. The caller makes a selection by either selecting "1" or "2". The caller's selection is examined at step S176. If the caller would like to submit another prescription request, then the appropriate selection is "1", and control passes to step S178. At step S178, the caller is informed that he or she will be required to submit information regarding the new prescription and control passes to step S112. If the caller decides not to enter any additional prescriptions, then control passes to step S180. The caller is informed that the prescription will be processed and received by the patient in approximately 5 to 7 business days.

Depending on the specific embodiment of the invention being implemented, the amount of time required to deliver the prescription to the patient can vary. For example, the caller may be provided with an option to request overnight delivery once the prescription has been filled. Alternatively, the caller may be provided with an option to request that the prescription be filled at a local pharmacy where the patient can physically go and pick up the medication.

FIGS. 6A–6E are flow diagrams illustrating an alternative implementation of the prescription processing system of the present invention. At step S210, a telephone connection is established between the caller and the prescription processing system. The caller is greeted and provided with instructions for selecting whether a prescription renewal is being submitted or a new prescription is being submitted. The caller makes a selection by either saying the word "1" to renew the prescription or saying the word "2" to submit a new prescription. Alternatively, the keys of the telephone keypad can be used to make the selection. At step S214, the caller's input is examined. If a new prescription is being submitted, then control passes to block A. If a prescription is being renewed, then control passes to step S216.

At step S216, the prescription processing system database is queried to identify the physician telephone or ANI number. This can be done in several ways. For example, the caller can be prompted to submit the telephone number of the physician's office, or the telephone number from which the caller has dialed can be automatically captured and compared to various telephone numbers stored on the database in order to obtain a cross-referenced match for the physician telephone or ANI number, and optionally the called number or DNIS number may also or alternatively be used. Alternatively the caller can be prompted to input this information. At step S218, the prescription processing system determines if the ANI number has been found. If it has been found, then control passes to step S220. If the ANI number cannot be found, then the caller is prompted to submit either the physician's DEA or fax number. At step S224, the database is again queried in order to search for the DEA or fax number. If the DEA or fax number is found, then control passes to step S220. If neither the DEA nor the fax number are found, then the caller is prompted at step S228 to say the physician's full name and telephone number. Control then returns to step S220.

The caller is prompted to submit the 12 digit number of the prescription being renewed. At step S230, the prescription processing system database is queried to locate the prescription number. If the prescription number cannot be found, then control passes to block B. If the prescription number is found, then a verification message is played for the caller at step S234 in order to confirm that the appropriate prescription number was submitted. At step S236, the caller provides an indication of whether he or she would like to accept the prescription number or resubmit a new prescription number. If the caller would like to resubmit the prescription number, then he or she can say or input the word "2" and control returns to step S220. If the prescription number is accepted, then control passes to step S238 where the caller is directed to the closings section. Callers who are submitting new prescription requests are directed to step S240 where the prescription processing system database is queried for the physician ANI number. As previously discussed, the ANI number can be submitted, cross-referenced, etc. Similar to the procedure for renewing prescriptions, if the ANI number is not found at step S242, then control passes to step S236. The caller is prompted to say the DEA or fax number of the prescribing physician.

At step S248, the prescription processing system database is queried to locate the DEA or fax number of the prescribing physician. If neither numbers are found at step S250, then the caller is prompted to say the physician's full name and telephone number at step S252. If either the physician ANI number or the DEA number or fax number is found, then control passes to step S244. Likewise, control passes to step S244 after the caller has submitted the physician's full name and telephone number. At step S244, the physician's information is embedded into an e-mail or appropriate file. At step S254, the caller is prompted to say the member ID number corresponding to the patient. Furthermore, if the prescription number was not found during a prescription renewal, the caller will also be directed to step S254. At step S256, the prescription processing system database is queried to locate the member ID number. If the member ID number is not found at step S258, then the caller is prompted to say the member's full name and zip code at step S260. If the member ID number is found, then control passes to S262. Control will also pass to step S262 after the caller has submitted the member's name and zip code. At step S262, the member and patient information is embedded into the e-mail or appropriate data file. At step S264, the caller submits the patient's full name, date of birth, and mailing address. At step S266, the prescription processing system writes administrative information to the data file. The administrative information can consist of any data that will later assist in the conversion and transcription of the files generated while receiving a prescription request. At step S268, the caller submits the actual prescription information. At step S270, the caller is informed that generic drugs will be substituted, as appropriate. If the caller does not wish to accept generic drugs, then this request can be made while submitting the prescription information.

At step S272, the recorded information is replayed for approval by the caller. At step S274, the caller can elect to accept the current recorded prescription information by either saying or pressing the word "1" or resubmit the prescription information by saying or pressing the word "2". If the caller would like to resubmit the prescription information, then control returns to step S268. If the caller is satisfied with the current prescription information, then control passes to step S276. The recordings and other files are then saved on the prescription processing system database in digital form. At step S278, the caller is directed to the closings section. The information saved on the prescription processing system for the prescription request can also be e-mailed, or otherwise transmitted, for storage to an appropriate queue in the database. The prescription requests can be subsequently accessed, for example, by a header entry agent for processing.

At step S280, the caller is asked if he or she would like to submit another prescription request. At step S282, the caller can elect to submit another prescription request by either saying or pressing the word "1". At step S284, the caller is informed that a new script will be required and control returns to step S212. The script corresponds to the dialogue/information submitted to generate the prescription request. The caller can also indicate that no additional prescription requests are desired by either saying or pressing the word "2". Control would then pass to step S286 where a parting greeting is played.

FIGS. 7A–7E are flow diagrams illustrating processing of prescription requests according to another exemplary embodiment of the present invention. At step S300, the caller (or appropriate personnel) establishes a connection with the prescription processing system. Once the connection is established, the caller is greeted with a message identifying the prescription processing system. In the event that a patient or member attempts to establish connection to the prescription processing system, a message can be optionally played to indicate that the line is for physician use only. Patients and members would have to call back and select a different option. Optionally, the message can give the caller a choice to be redirected to a different (or patient/member) menu. At step S302, an optional message indicating that prescriptions for controlled medications cannot be accepted via the prescription processing system is played for the physician.

At step S304, the caller is asked whether he or she is renewing an existing prescription or requesting a new prescription. If the caller is renewing a prescription, he or she can select this option by either saying the word "1", or pressing the "1" key on the telephone keypad. To submit a new prescription, the caller can either say the word "2" or press the number "2" on the telephone keypad. Accordingly, it should be appreciated that a voice responsive system should be available to interpret the selection when the caller speaks the desired commands. Regardless of the selection, control will proceed to step S306. However, the prescription processing system will store the selection in order to tailor subsequent messages and questions to the caller.

At step S306, the caller is prompted to say his or her full name and official (or office) title. Preferably, the "#" key can be pressed to provide an indication that the caller has finished saying the requested information. Alternatively, it should be noted that the prescription processing system can be configured to detect when the caller has completed saying the information based on a predetermined period of vocal inactivity. At step S308, the caller is prompted to say the prescribing physician's full name, telephone number, and office address. At step S310, the caller is prompted to enter the member ID number. The caller is also given an option to bypass this step by pressing the "#" key on the telephone keypad if he or she does not know the member ID number.

At step S312, the caller is prompted to say the member's full name and zip code. At step S314, the caller says the full name and date of birth of the patient. At step S316, the caller says the patient's mailing address. Depending on whether the caller had elected to renew or submit a new prescription, a different series of questions will follow. For a renewal, control passes to step S318. The caller is prompted to submit the number of the prescription to be renewed. The caller is optionally instructed to press the "#" key on the telephone keypad if he or she does not know the prescription number. If the caller does not know the prescription number, then control passes to step S326. At step S320, the caller is prompted to indicate whether or not there will be a change in therapy for the prescription being renewed. If there is a change in therapy, the caller can either say the word "yes" or press the "1" key on the telephone keypad. If, on the other hand, there is no change in therapy, then the caller can say the word "no" or press the "2" key on the telephone keypad. A change in therapy transfers control to step S328, while no change in therapy allows the process to continue to step S322. The caller can also cancel the current transaction by saying the word "3" or pressing the "3" key on the telephone keypad. Control would subsequently pass to block A.

At step S322, the caller is informed that the prescription will be renewed. The caller must also provide an input that is indicative of whether or not he or she would like to confirm renewal of the prescription, or cancel the current prescription renewal. If the transaction is to be cancelled, then control would again pass to block A. Otherwise, if the prescription will be renewed, then control passes to step S324. At step S324, the caller is asked to submit the drug name and strength for the prescription being renewed. Control then proceeds to step S330.

Returning to step S316, if the caller had elected to submit a new prescription, control would have branched to step S326. The caller is informed that generic versions of the drug will be substituted, unless indicated otherwise. The caller is also prompted to indicate the number of prescriptions that will be submitted. At step S328, the caller is prompted to say the prescription information. The caller is also reminded to include information such as the medication name, the strength, the quantity, directions, and refill instructions. Furthermore, the caller is informed that the medication can be prescribed for a period of up to 90 days, with three subsequent refills.

At step S330, the prescription processing system replays the recorded prescription information in order to obtain approval from the caller. The caller can accept the recorded prescription information by saying the word "1" or pressing the "1" key on the telephone keypad. The caller can elect to re-record the prescription information by saying the word "2" or pressing the "2" key on the telephone keypad. Finally, the caller can cancel the transaction by saying the word "3" or pressing the "3" key on the telephone keypad. If the caller elects to cancel the transaction, control passes to block A. At block A, the caller is directed to step S336 and informed that the transaction has been cancelled. Control then passes to step S332. If the caller would like to resubmit the prescription information, then control passes to step S334. The caller is advised that he or she must resubmit the prescription information and control returns to step S328.

At step 332, the caller is asked if he or she would like to submit another prescription. If the caller would like to submit another prescription request, then control passes to step S338. At step S338, the caller is informed that he or she will be required to submit information regarding the new prescription and control returns to step S304. Control can also pass to step S310, depending on certain optional embodiments of the invention. If the caller decides not to enter additional prescriptions, then control passes to step S340. The caller is informed that the prescription will be processed and received by the patient in approximately 7 to 10 business days.

Figure 8:
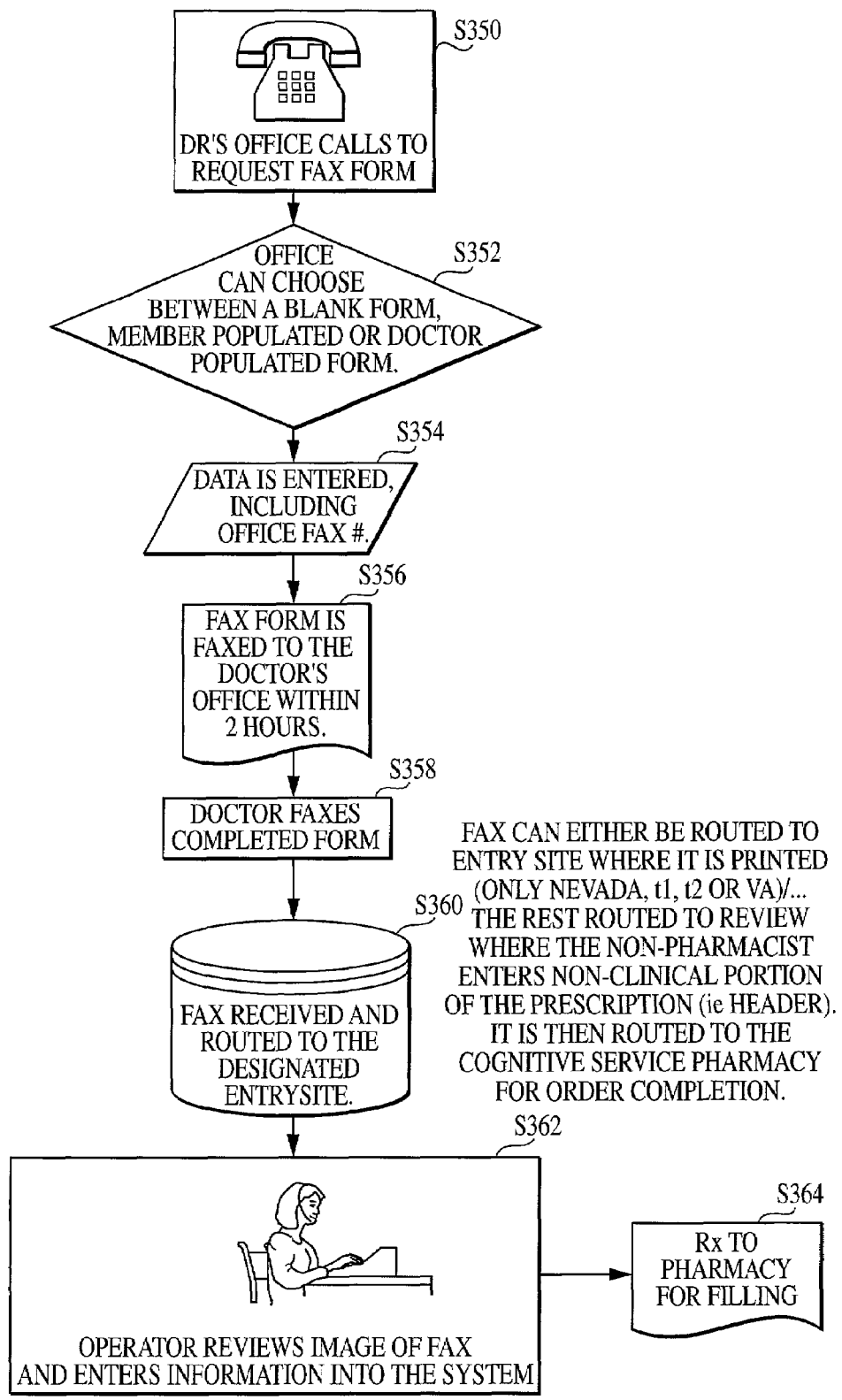
FIG. 8 is a flow diagram illustrating another embodiment of the present invention for processing prescription requests.

FIG. 8 is a flow diagram illustrating another embodiment of the present invention for processing prescription requests. At step S350, a telephone call is initiated from the physician's office to the prescription processing system. Alternatively, a dedicated call processing center for receiving calls from the physician can be established as part of the prescription processing system. At step S352, a connection is established with the prescription processing system. The physician is given an option to select between either a blank form, a member populated form, or a physician populated form. The form is used for producing a tangible copy of the prescription request, as will be described in greater detail hereinbelow.

For example, if a blank form is requested, there will be no patient information or physician information written on the form when it is provided to the physician. If a member populated form is selected, then the physician will receive a form that contains information which has been previously supplied by the member. Likewise, a doctor populated form contains information about the physician and the patient which has been previously submitted by the physician. It should be noted, however, that certain situations can necessitate that the physician select a particular type of form. For example, if the physician does not have any information on file and the member for whom the prescription request is being submitted is a new member, then there will be insufficient information for populating the form. Consequently, the physician must request a blank form.

At step S354, the physician is prompted to submit certain information about the member, patient, etc. Furthermore, the physician must enter an office fax number. The information can be entered in a variety of ways including, as previously described, through the telephone keypad or normal speech. Once the data has been submitted, the pre-populated information previously stored in the prescription processing system database is entered into a prescription fax form. The prescription fax form is then faxed to the physician's office. The physician will be required to subsequently enter specific details regarding the medication, patient history, etc. into the prescription fax form. Furthermore, the physician can submit a signature on the fax form.

Figure 9:
FIG. 9 is an illustration of a sample prescription fax form that can be used with certain embodiments of the present invention.

Referring additionally to FIG. 9, according to one embodiment of the present invention, the prescription fax form can include a designated section wherein the physician can attach an actual copy of the prescription form. As shown herein, the prescription fax form has numerous labels that identify corresponding fields. The illustrated prescription fax form is a blank form and contains no information regarding the patient or the physician within most of the fields. The only information contained on the fax form is the office fax number for the physician. This is the only necessary information as the prescription fax form must be faxed to the physician's office. The prescription fax form contains various fields for the physician to enter information necessary to process the prescription. In addition, a designated section is provided for the physician to affix the actual prescription form to the prescription fax form.

At step S358, the physician faxes the completed prescription fax form to the prescription processing system. The fax form is received, and prepared for routing to an appropriate filling pharmacy at step S360. At step S362, an operator such as a medical personnel, pharmacist, or physician located with respect or access to the prescription processing system reviews the information contained on the prescription fax form and enters the information into the database of the prescription processing system. The prescription fax form is then routed to the appropriate pharmacy where the prescription will be filled at step S364. Once the prescription has been filled, the medication is submitted to the patient. As previously discussed, this can be accomplished either through conventional product delivery channels such as the United States Postal Service or specialized couriers. Alternatively, the prescription fax form can be routed to a pharmacy that is conveniently accessible to the patient. Once the prescription is filled, the patient would simply go the local pharmacy and obtain the medication.

Figure 10A:
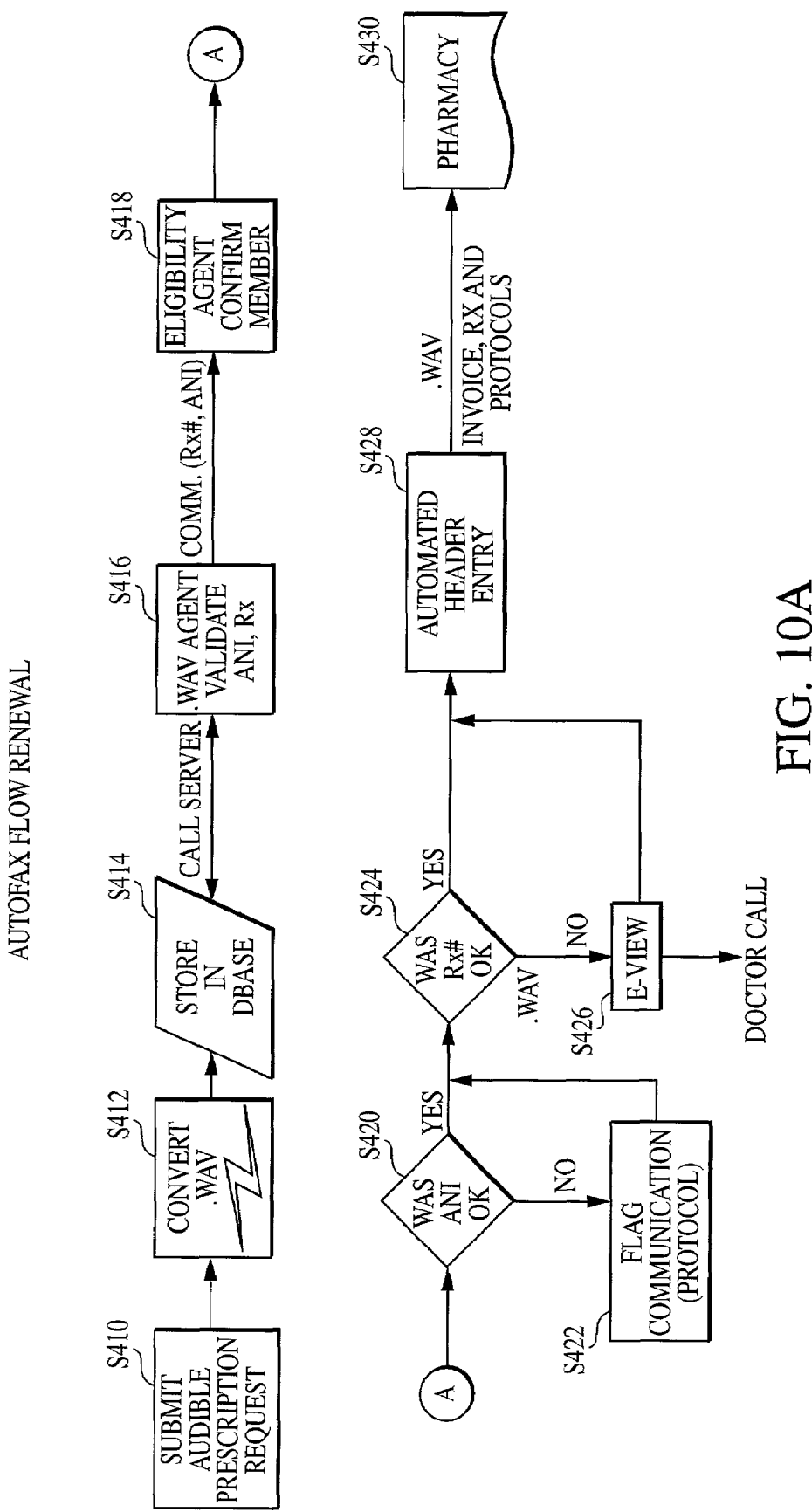
FIG. 10A is a flow diagram illustrating renewal of prescription requests according to another embodiment of the present invention.

FIG. 10A is a flow diagram which illustrates renewal of prescription requests according to another embodiment of the present invention. At step S410, the physician contacts the prescription processing system and submits the audible prescription request. The audible, or other data, prescription request is captured in the form of a digital audio file, as previously described. At step S412, the digital audio file is converted to a data file using various processing techniques such as, for example, computer-aided voice recognition processing. Once the digital audio file has been converted to a data file, the data file is stored in the prescription processing system database at step S414.

At step S416, the prescription processing system receives and validates the physician's ANI number and the prescription number that he or she would like to renew. At step S418, the prescription processing system validates the member's (or patient's) eligibility to participate in the program. As previously stated, the member's eligibility will depend on the particular insurance carrier being used and whether the insurance carrier has previously negotiated to utilize the prescription processing system. At step S420, the prescription processing system reviews the ANI number to verify that there is a match currently on file for the physician. If there is no corresponding match on record for the physician, then control passes to step S422. At step S422, a communication flag is raised in order to alert an appropriate personnel such as an operator, technician, pharmacist, and/or medical doctor, of the prescription processing system to initiate contact with the physician and verify the information that was previously submitted. Otherwise, if there is a current match on record for the physician's ANI number, then control passes to step S424.

The prescription number being renewed is queried against the database to locate the existing prescription. If the existing prescription cannot be located in the database, then control passes to step S426. At step S426, a header entry agent will review the information submitted by the physician (both the digital audio file and the data file, if necessary) in order to determine whether errors have been encountered in the data translation phase of step S412. The header entry agent may find it necessary to contact the physician if the original prescription number still cannot be located in the database. If the prescription number is located, then control passes to step S428. At this point, all of the information necessary to complete the prescription request form is automatically retrieved from the database of the prescription processing system and entered into a prescription request form. The completed prescription request form is subsequently transmitted to the pharmacy to be filled at step S430.

Figure 10B:
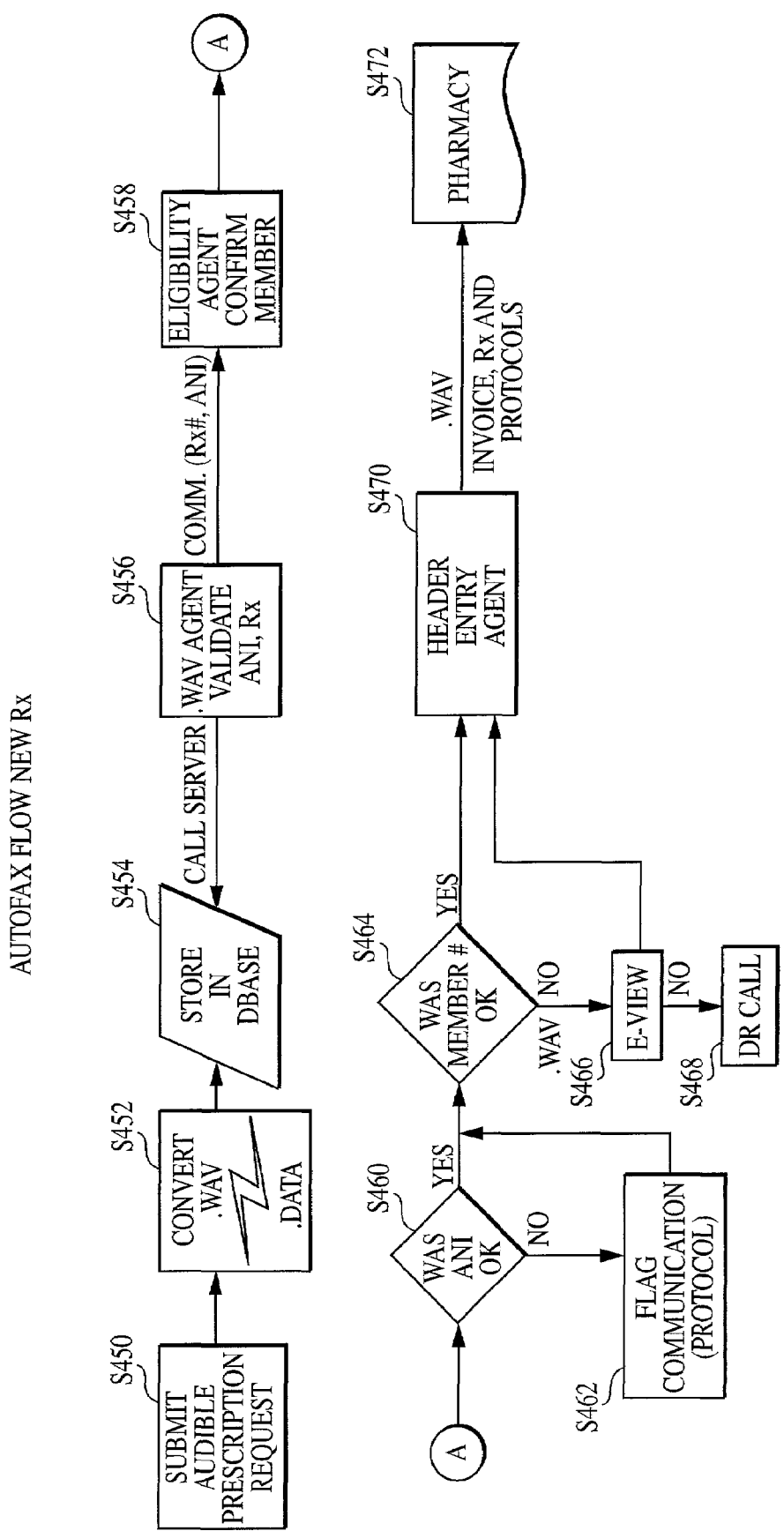
FIG. 10B is a flow diagram illustrating the processing of new prescription requests according to another embodiment of the present invention.

FIG. 10B illustrates the process for submitting new prescription requests. At step S450, the physician contacts the prescription processing system and submits the audible, or other form, prescription request. At step S452, the digitized audio prescription request is converted into a data file. At step S454 the data file is stored on the database of the prescription processing system. At step S456, the ANI number and prescription number are validated by the prescription processing system. At step S458, the members' eligibility for using the prescription processing system is checked. At step S460, the physician ANI number is used to query the database to determine whether there is a record of the ANI number. If there is no existing record, then a communication flag is raised in order to alert, for example, a header entry agent to review the information and possibly initiate contact with the physician. If there is an existing ANI number, then the member ID number is used to query the database. If there is no existing member ID number on record, then the header entry agent will review the information submitted in order to verify that no errors have occurred. If the member ID number still cannot be located, then the physician will be contacted in order to provide this information. Once the member ID number is located, the existing information for the prescription is forwarded to a header entry agent at step S470 in order to prepare a completed prescription request form. The prescription request form is subsequently sent to the pharmacy at step S472 in order to fill the prescription.

Hardware Description

Figure 11:
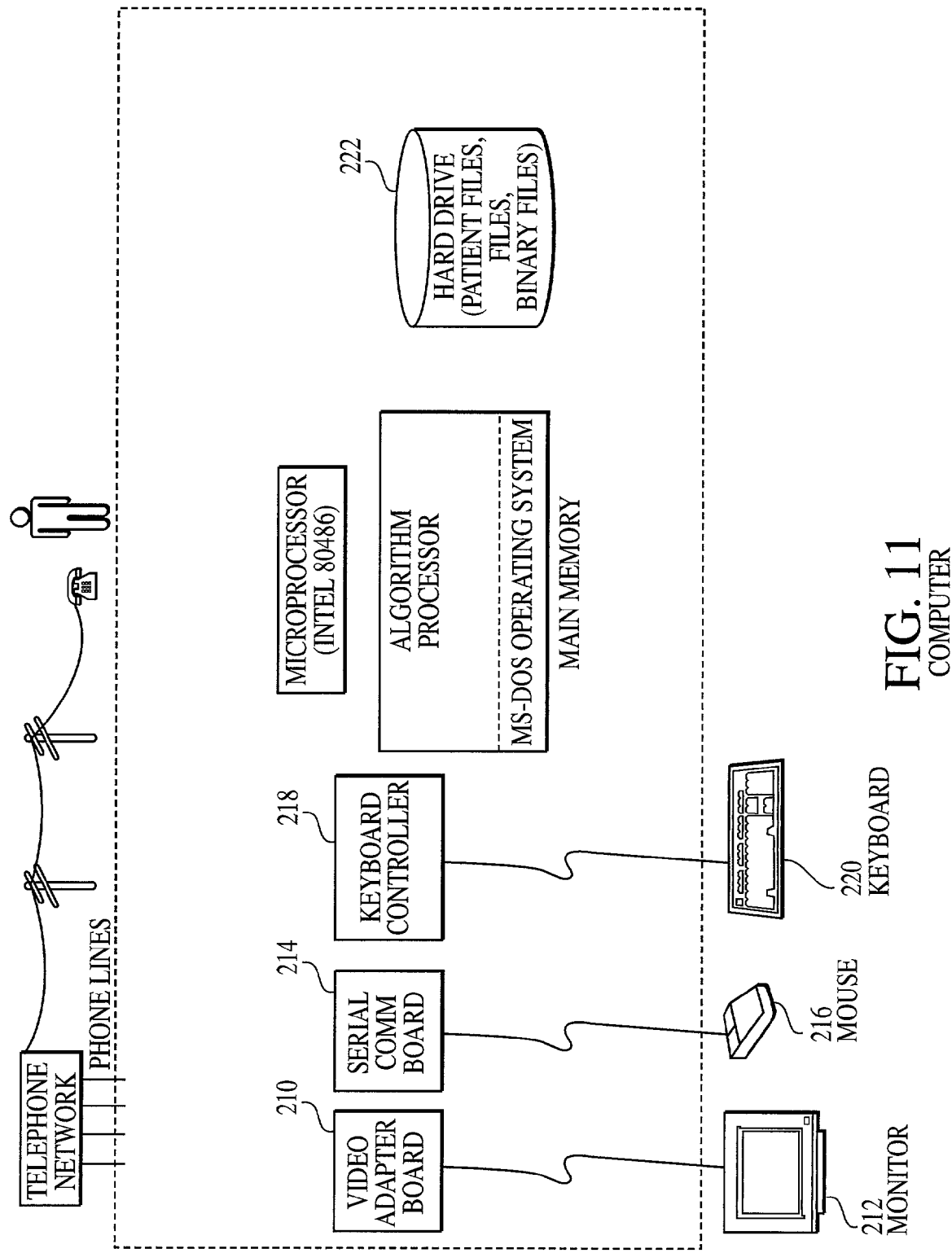
FIG. 11 is an illustration of a computer system and telephone network suitable for use in implementing and/or assisting in implementing the present invention.
Figure 12:
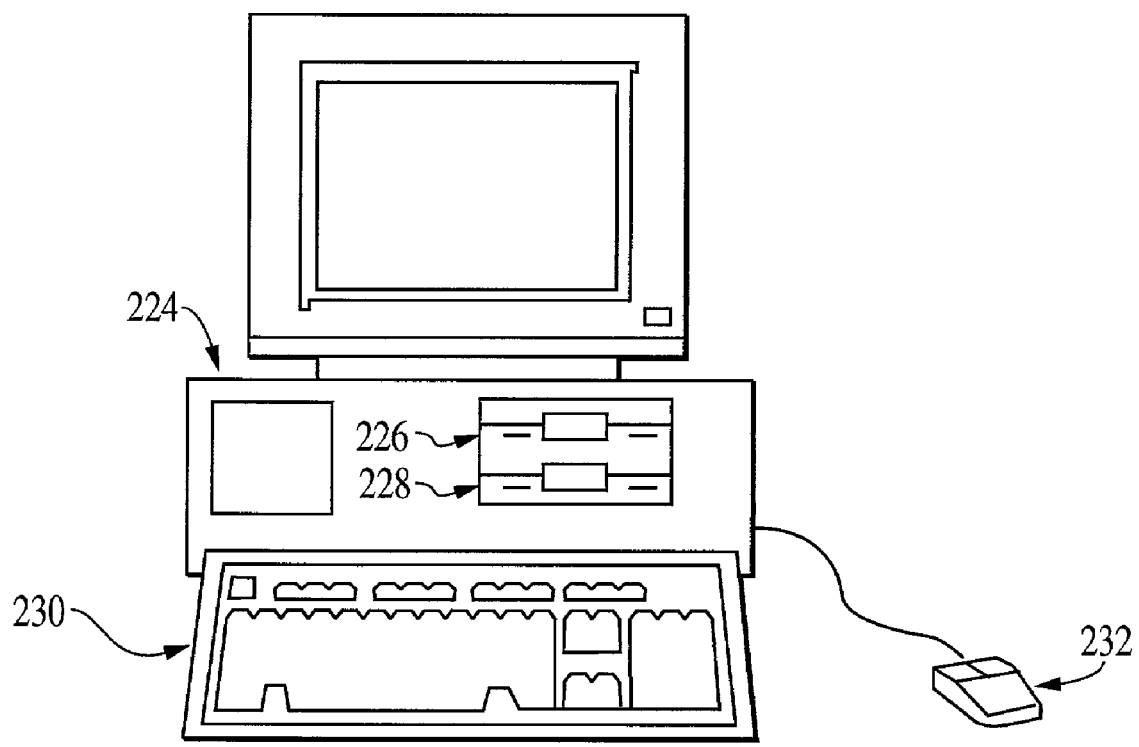
FIG. 12 illustrates a computer type suitable for implementing and/or assisting in implementation the present invention.
Figure 13:
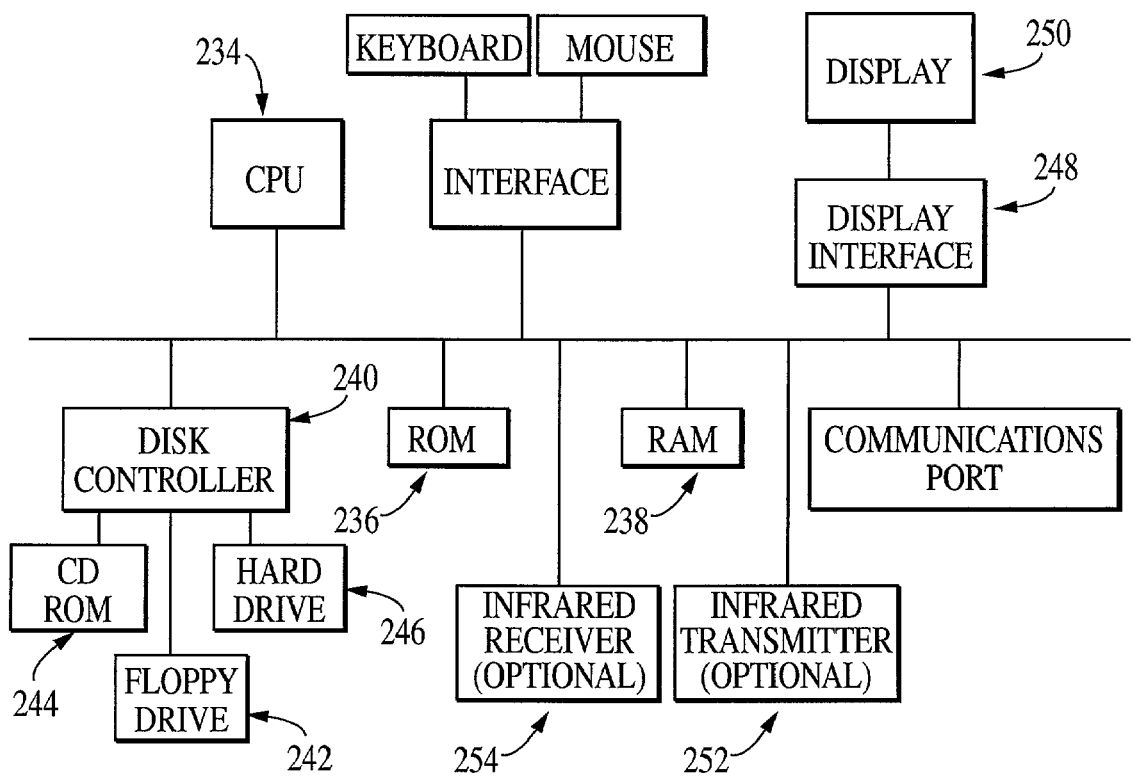
FIG. 13 is a block diagram of the conceptual flow of the computer assisted process in accordance with the present invention.
Figure 14:
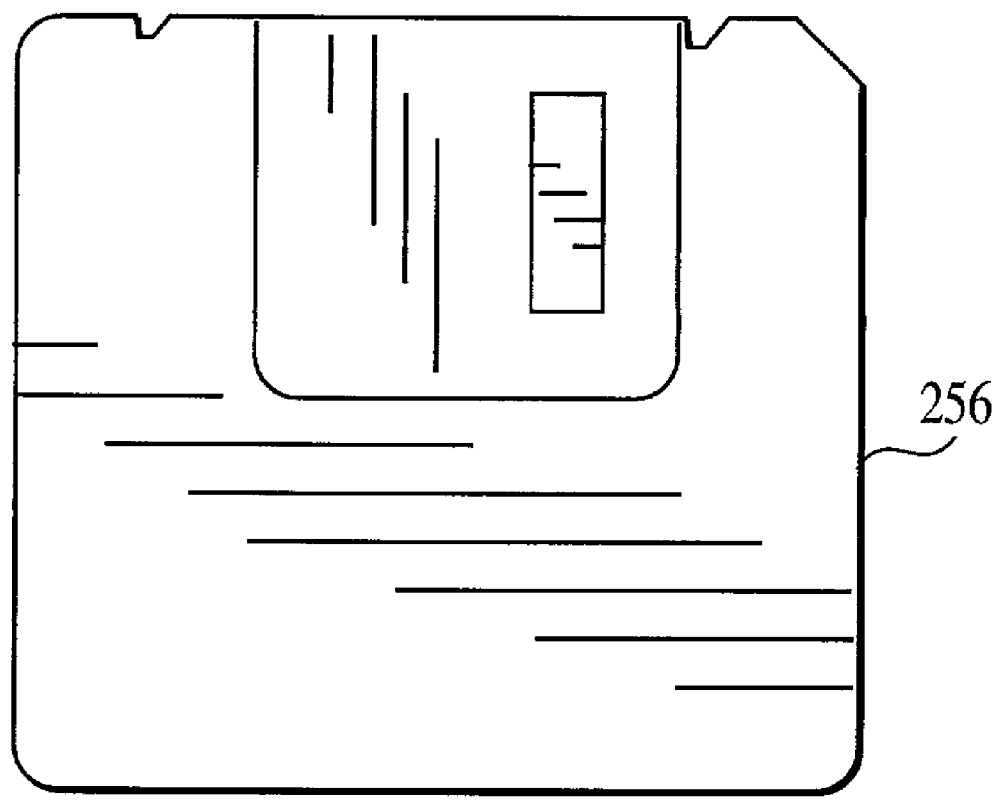
FIG. 14 is an exemplary memory medium which can be used with the computer illustrated in FIGS. 12 and 13.

FIG. 11 is an illustration of the computer system and telephone network used in several embodiments of the invention. FIG. 12 is an illustration of another computer of the type suitable for use in the invention. FIG. 13 is a block diagram of standard computer components that make up a standard computer and that may be used in the invention. FIG. 14 is a conceptual view of the memory storage medium.

Hardware Configurations

FIG. 11 is a block diagram of the hardware design of a computer of the type that can be used in the invention. A video adapter board 210, preferably at VGA or better resolution, interconnects to a video monitor 212. A serial communication circuit 214 interfaces a pointing device, such as a mouse 216. A parallel communication circuit may be used in place of circuit 214 in another embodiment. A keyboard controller circuit 218 interfaces a keyboard 220. A small computer systems interface (SCSI) adapter provides a SCSI bus to which, for example, a 100 Gb or greater hard disk drive is attached. The hard drive 222 stores database files such as the patient files, drug utilization files, and demographic files.

FIG. 12 illustrates another personal computer of the type suitable for carrying out the invention. Viewed externally, the conceptual computer system in FIG. 12 has a central processing unit 224 having disk drives. Disk drive indications 226, 228 are merely symbolic of a number of disk drives which might be accommodated by the computer system. Typically these would include a floppy disk drive 226, a hard disk drive (not shown externally), and a CD ROM. The number and type of drives varies, typically with different computer configurations. Disk drives are in fact optional, and for space considerations, may easily be omitted from the computer system used in conjunction with the processes described herein.

The computer also has an optional display upon which information is displayed. In some situations, a keyboard 230 and a mouse 232 may be provided as input devices to interface with the central processing unit. Then again, for enhanced portability, the keyboard may be either a limited function keyboard or omitted in its entirety. In addition, mouse may be a touch pad control device, or a track ball device, or even omitted in its entirety as well. In addition, the computer system also optionally includes at least one infrared transmitter and/or infrared receiver for either transmitting and/or receiving infrared signals, one example of wireless transmission and/or reception.

FIG. 13 illustrates a block diagram of the internal hardware of the computer of FIG. 12. A bus serves as the main information highway interconnecting the other components of the computer. CPU 234 is the central processing unit of the system, performing calculations and logic operations required to execute a program. Read only memory (ROM) 236 and random access memory (RAM) 238 constitute the main memory of the computer. Disk controller 240 interfaces one or more disk drives to the system bus. These disk drives may be floppy disk drives 242 or CD ROM 244 or DVD (digital video disks) drives such as, internal or external hard drives 246. As indicated previously, these various disk drives and disk controllers are optional devices.

A display interface 248 interfaces the display 250 and permits information from the bus to be displayed on the display 250. Again as indicated, the display is also an optional accessory. For example, the display could be substituted or omitted from the device, and a display on the telephone may be used to display information. Communication with external devices occurs utilizing, for example, the communication port or standard wireless devices.

In addition to the standard components of the computer, the computer also optionally includes an infrared transmitter 252 and/or infrared receiver 254. Infrared transmitter is utilized when the computer system is used in the process described herein. Infrared receiver is generally utilized when the computer system is used in conjunction with the telephone that is to receive the infrared signal. Instead of utilizing an infrared transmitter or infrared receiver, the computer system could use at least one of a low power radio transmitter and/or a low power radio receiver. The low power radio transmitter transmits the signal for reception by another low power radio receiver. The low power radio transmitter and/or receiver are standard devices in industry.

Additionally, the computer system can be provided with an optional security layer (not shown) to prevent unauthorized access data and hardware. Security layers may also be included in the communication between the physician and pharmacist or between the pharmacist and filling pharmacy to protect privacy or for other reasons (e.g., preventing theft or fraud). The security layer includes any standard security scheme or technology, such as standard decryption technology, and may be used system wide as well, for example, with all workstations, pharmacist, physicians, and the like. As described above, the present invention does not require the direct interaction with the various computers, but provides this additional feature to further facilitate the communication process between various work station personnel, and the like.

FIG. 14 is an illustration of an exemplary memory medium 256 which can be used with disk drives illustrated in FIGS. 12 and 13. Typically, memory media such as floppy disks, a CD ROM, or a digital video disk will contain, for example, a multi-byte locale for a single byte language and the program information for controlling the computer to enable the computer to perform the functions described herein. Alternatively, ROM 236 and/or RAM 238 illustrated in FIG. 13 can also be used to store the program information that is used to instruct the central processing unit to perform the operations associated with the present invention.

Major objectives and advantages of the present invention are convenience and cost reduction (where appropriate, safe, and effective). The prescription processing network stands to benefit physicians, pharmacists, and patients. More particularly, a physician's time can be efficiently spent treating patients, and prescription requests can be submitted when such an action will not adversely effect the time available to treat patients. Furthermore, pharmacists can focus his or her time and attention to accurate preparation of prescriptions without interruption. Patients also benefit in several ways. First, scheduled appointments are easier to maintain. The quality of care received is improved because the physician's time is not wasted on other tasks, such as submitting prescription requests. Furthermore, costs are reduced because of the improved efficiency realized by the physician and pharmacist.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of processing prescription requests comprising the steps:
  establishing a connection to a remotely located prescription processing system;
  submitting a prescription request to the prescription processing system;
  capturing the prescription request for subsequent manipulation;
  converting the captured prescription request to a digitized format at the prescription processing system to obtain a digitized prescription request;
  storing the digitized prescription request on a database maintained by the prescription processing system transcribing the captured prescription request;
  independently assessing by personnel associated with the prescription processing system correctness of the prescription request, said personnel comprising a non-physician user electronically signing a patient's orders resulting from said independently assessing;
  preparing by said personnel a completed prescription form based on the submitted prescription request;
  sending the completed proscription form to a filling pharmacy; and
  filling the prescription request, at the filling pharmacy, based on the completed prescription form.

2. The method claim 1, wherein the prescription request is submitted in audible form.

3. The method of claim 1, wherein the prescription request is submitted by facsimile.

4. The method of claim 1, wherein the prescription request is submitted by electronic mail.

5. The method of claim 1, wherein the prescription request is submitted in the form of data from a wireless/mobile device.

6. The method of claim 1, wherein the prescription request is submitted in the form of data transmitted from a PDA.

7. The method of claim 1, wherein the step of preparing is performed based, at least partially, on a content of the transcribed prescription request.

8. The method of claim 1, wherein the digitized format is a digital data format.

9. The method claim 1, wherein the digitized format is a standard digital audio format.

10. The method of claim 1, further comprising the steps;
  creating an identification file, including identification data, for the digitized prescription request; and
  concatenating the identification file with the digitized prescription request to form a prescription tile.

11. Thy method of claim 1, further comprising a step of prompting a user to input information associated with the prescription.

12. The method of claim 11, wherein the step of prompting comprises the steps:
  requesting physician information;
  requesting user information; and
  requesting a member ID number.

13. The method of claim 11, further comprising a step of verifying the prompted information input by the user.

14. The method of claim 13, further comprising the steps:
  printing a form pre-populated with the verified information;
  assigning the form a unique identifier which associates the form with the prescription request; and
  submitting the pre-populated form to the user via facsimile.

15. The method of claim 12, further comprising the steps:
  comparing, at the prescription processing system, a physician's phone number and a prescription number; and
  if the physician's phone number and the prescription number result in a predetermined relationship, wherein the predetermined relationship is a match between the physician's phone number and the prescription number and a stored physician's phone number and a stored prescription number stored at the prescription processing system then filling the prescription request using an automated entry agent associated with the prescription processing system.

16. The method claim 15, wherein, if the physician's phone number and the prescription number fails to result in a predetermined relationship, the method further comprises contacting a user to indicate the failure and to determine whether the prescription request is authentic.

17. The method of claim 1, wherein the step of submitting includes a step of determining if the prescription request is to renew an existing prescription or to submit a new prescription.

18. The method of claim 17, wherein the prescription request is to submit a new prescription, and further comprising the steps:
   submitting member information;
   submitting patient information; and
   submitting medication information.

19. The method of claim 18, wherein the member information includes the member's name and the member's address.

20. The method of claim 17, wherein the prescription request is to renew a prescription and further comprising the steps:
   determining if there is an existing unique prescription number for renewal; and
   requesting the existing unique prescription number if it is available.

21. The method of claim 20, further comprising the steps:
   determining if there is a change in patient therapy that would affect one or more aspects of the prescription request; and
   if there is no change inpatient therapy, then performing the steps:
      reviewing the submitted prescription request to obtain the user's approval, and
      closing the prescription request.

22. The method of claim 21, wherein the user does not approve the submitted prescription request based on the step of reviewing, and further comprising a step of canceling the prescription request.

23. The method of claim 21, wherein there is a change in therapy, and further comprising the steps:
   requesting new medication information from the user; and
   reviewing the new medication information.

24. The method of claim 20, wherein there is no prescription number for renewal, and further comprising the steps:
   requesting member information;
   requesting patient information; and
   requesting medication information.

25. The method of claim 24, wherein the member information requested about the member includes the member's name and the member's address.

26. The method of claim 1, further comprising a step of closing the prescription request.

27. The method of claim 26, wherein the step of closing comprises the steps:
   determining if the user would like to submit a new prescription request;
   repeating the steps of submitting, preparing, sending, and filling if the user would like to submit a new prescription request; and
   terminating the connection if the user would not like to submit a new prescription request.

28. The method of claim 1, wherein the step of establishing includes a step of establishing the connection using a telephone and wherein the step of submitting includes communicating with the prescription processing system using a touch tone telephone keypad.

29. The method of claim 1, wherein the step of connecting includes a step of establishing the connection over an electronic network using a personal computer.

30. The method of claim 29, wherein the electronic network is a direct-connection network.

31. The method of claim 29, wherein the electronic network is a packet-switched network.

32. The method of claim 29, wherein:
   the prescription request is an audible prescription request; and
   the step of submitting includes a step of submitting the audible prescription request through a microphone coupled to the personal computer.

33. The method of claim 1, wherein the step of submitting a prescription request includes the steps:
   submitting patient information; and
   submitting medication information.

34. The method of claim 33, wherein the submitted patient information includes a patient name, address, and date of birth.

35. The method of claim 33, wherein the submitted medication information includes medication name, strength, and dosage.

36. The method of claim 1, wherein the prescription request is submitted telephonically.

37. The method of claim 1, wherein the prescription request is submitted using computerized voice entry techniques.

38. A method of processing prescription requests comprising the steps:
   establishing a connection to a remotely located prescription processing system;
   submitting a prescription request to the prescription processing system;
   capturing the prescription request for subsequent manipulation;
   processing the captured prescription request;
   independently assessing by at least one of a pharmacist and personnel associated with the prescription processing system correctness of the prescription request, said personnel comprising a non-physician user electronically signing a patient's orders resulting from said independently assessing;
   comparing, at the prescription processing system, a physician's phone number and a prescription number;
   preparing, by said at least one of a pharmacist and personnel a completed prescription form based, at least partially, on the processed prescription request;
   sending the completed prescription form to a predetermined pharmacy; and
   when the physician's phone number and the prescription number result in a predetermined relationship, wherein the predetermined relationship is a match between the physician's phone number and the prescription number and a stored physician's phone number and a stored prescription number stored at the prescription processing system then filling the prescription request, at the predetermined pharmacy, based on the completed prescription form.

39. A method of processing prescription requests comprising the steps:
   establishing a connection to a remotely located prescription processing system;

submitting a prescription request to the prescription processing system;
capturing the prescription request;
converting the captured prescription request to a digitized format to obtain a digitized prescription request;
creating an identification file, including identification data, for the digitized prescription request;
associating the identification file and the digitized prescription request to form a prescription file;
storing the prescription file on a database maintained by the prescription processing system;
transcribing the digitized prescription request;
independently assessing by at least one of a pharmacist and personnel associated with the prescription processing system correctness of the prescription request, said personnel comprising a non-physician user electronically signing a patient's orders resulting from said independently assessing;
preparing, by said at least one of a pharmacist and personnel a completed prescription form based, at least partially, on the processed prescription request;
sending the completed prescription form to a filling pharmacy; and
filling the prescription request, at the filling pharmacy, based at least partially on the completed prescription form.

40. A method of processing prescription requests comprising the steps:
establishing a connection to a remotely located prescription processing system;
submitting a prescription request to the prescription processing system;
capturing the prescription request;
converting the captured prescription request to a digitized format to obtain a digitized prescription request;
creating an identification file, including identification data, for the digitized prescription request;
associating the identification file and the digitized prescription request to form a prescription file;
storing the prescription file on a database maintained by the prescription processing system;
transcribing the captured prescription request;
independently assessing by at least one of a pharmacist and personnel associated with the prescription processing system correctness of the prescription request;
preparing, by said at least one of a pharmacist and personnel a completed prescription form based, at least partially, on the processed prescription request;
sending the completed prescription form to a pharmacy;
filling the prescription request, at the pharmacy, based on the completed prescription form;
determining when the user would like to submit a new prescription request;
repeating the steps of submitting, capturing, transcribing, preparing, sending, filling, and determining when the user would like to submit a new prescription request; and
terminating the connection when the user would not like to submit a new prescription request.

41. A method of processing prescription requests comprising the steps:
establishing a connection to a remotely located prescription processing system;
submitting a prescription request to the prescription processing system, wherein the prescription request includes user information and a member ID number;
capturing the prescription request;
converting the captured prescription request to a digitized format to obtain a digitized prescription request;
creating an identification file, including identification data, for the digitized prescription request;
associating the identification file with the digitized prescription request to form a prescription file;
storing the prescription file on a database maintained by the prescription processing system;
transcribing the digitized prescription request;
independently assessing by at least one of a pharmacist and personnel associated with the prescription processing system correctness of the prescription request;
preparing, by said at least one of a pharmacist and personnel a completed prescription form based, at least partially, on the processed prescription request;
sending the completed prescription form to a central pharmacy; and
filling the prescription request, at the central pharmacy, based at least partially on the completed prescription form.

42. A method of submitting a prescription request for retrieval of a filled prescription by a patient, the method comprising the steps:
initiating a connection to a remotely located prescription processing system;
submitting an audible prescription request to the prescription processing system;
capturing the prescription request;
converting the captured prescription request to a digitized format to obtain a digitized prescription request;
creating an identification file, including identification data for the digitized prescription request;
associating the identification file and the digitized prescription request to form a prescription file;
storing the prescription file on a database maintained by the prescription processing system;
transcribing the digitized prescription request;
filling the prescription request, at a filling pharmacy responsive to receipt of the prescription request from the remotely located prescription processing system; and
retrieving, by the patient, a filled prescription from a predetermined filling pharmacy remotely located from the prescription processing system.

43. A method of processing a submitted prescription request, comprising the steps:
receiving a request from a remote source to establish a connection with a local prescription processing system;
establishing a connection with the remote source;
receiving an audible prescription request;
preparing, by a pharmacist, a completed prescription form based, at least partially, on the audible prescription request;
sending the completed prescription form to a pharmacy to be filled; and
when the physician's phone number and the prescription number result in a predetermined relationship, wherein the predetermined relationship is a match between the physician's phone number and the prescription number and a stored physician's phone number and a stored prescription number stored at the prescription processing system then filling the prescription request, at the predetermined pharmacy, based on the completed prescription form.

44. A prescription processing network comprising:
  a prescription processing system;
  a communication device for establishing a communication channel with said prescription processing system and submitting a prescription request over said communication channel, said communication device being remotely located from said prescription processing system;
  said prescription processing system being accessible by one of a pharmacist and personnel capable of independently assessing correctness of the prescription request for preparing a completed prescription form based, at least in part, on the submitted prescription request, and said prescription processing system includes a header entry agent for retrieving general information from a digitized prescription request, wherein said submitted prescription is digitized into said digitized prescription request, and transcribing said general information, wherein said general information comprises non-medication related information comprising at least one of member's name, member's identification number, physician information, and patient information; and
  a pharmacy for receiving said completed prescription form, and filling said prescription request based on the completed prescription form.

45. The prescription processing network of claim 44, wherein said communication device includes circuitry for submitting said prescription request electronically.

46. The prescription processing network of claim 44, wherein said communication device includes circuitry for submitting said prescription request in an audible format.

47. The prescription processing network of claim 44, wherein said communication channel is established over a private network.

48. The prescription processing network of claim 44, wherein said communication channel is established over a public network.

49. The prescription processing network of claim 48, wherein said public network is the Internet.

50. The prescription processing network of claim 44, wherein said communication device is a computer.

51. The prescription processing network of claim 44, wherein said communication device is a telephone.

52. The prescription processing network of claim 44, wherein said communication device is a facsimile device.

53. The prescription processing network of claim 44, wherein said pharmacist and said pharmacy are remotely located from each other, and remotely located from both said prescription processing system and said communication device.

54. The prescription processing network of claim 44, wherein said communication device includes circuitry for submitting said prescription request in an audible format using a telephone.

55. A method of processing prescription requests comprising the steps:
  establishing a connection to a remotely located prescription processing system using a telephone;
  submitting an audible prescription request to the prescription processing system using said telephone;
  retrieving general information using a header entry agent from a digitized prescription request;
  digitizing said submitted prescription into sad digitized prescription request;
  transcribing said general information comprising non-medication related information including at least one of member's name, member's identification number, physician information, and patient information
  independently assessing by personnel associated with the prescription processing system correctness of the prescription request;
  preparing by said personnel a completed prescription form based on the submitted prescription request;
  sending the completed prescription form to a filling pharmacy; and
  filling the prescription request, at the filling pharmacy, based on the completed prescription form.

56. A method of processing prescription requests comprising the steps:
  establishing a connection to a remotely located prescription processing system using a telephone;
  submitting an audible prescription request to the prescription processing system using said telephone;
  capturing the prescription request for subsequent manipulation;
  processing the captured prescription request;
  converting the captured prescription request to a digitized format to obtain a digitized prescription request;
  creating an identification file, including identification data, for the digitized prescription request;
  associating the identification file and the digitized prescription request to form a prescription file;
  storing the prescription file on a database maintained by the prescription, processing system transcribing the digitized prescription request;
  independently assessing by personnel associated with the prescription processing system correctness of the prescription request;
  preparing by said personnel a completed prescription form based on the submitted prescription request;
  sending the completed prescription form to a predetermined pharmacy; and
  filling the prescription request, at the predetermined pharmacy, based on the completed prescription form responsive to receipt of the prescription request from the remotely located prescription processing system.

57. A method of processing prescription requests comprising the steps:
  establishing a connection to a remotely located prescription processing system using a telephone;
  submitting an audible prescription request to the prescription processing system using said telephone;
  capturing the prescription request;
  converting the captured prescription request to a digitized format to obtain a digitized prescription request;
  creating an identification file, including identification data, for the digitized prescription request;
  associating the identification file and the digitized prescription request to form a prescription file;
  storing the prescription file on a database maintained by the prescription processing system;
  transcribing the digitized prescription request;
  independently assessing by personnel associated with the prescription processing system correctness of the prescription request;
  preparing by said personnel a completed prescription form based on the submitted prescription request;
  sending the completed prescription form to a filling pharmacy; and
  filling the prescription request, at the filling pharmacy, based at least partially on the completed prescription form.

58. A method of processing prescription requests comprising the steps:
  establishing a connection to a remotely located prescription processing system using a telephone;
  submitting an audible prescription request to the prescription processing system using said telephone;
  capturing the prescription request;
  transcribing the captured prescription request;
  converting the captured prescription request to a digitized format to obtain a digitized prescription request;
  creating an identification file, including identification data, for the digitized prescription request;
  associating the identification file and the digitized prescription request to form a prescription file;
  storing the prescription file on a database maintained by the prescription processing system;
  independently assessing by personnel associated with the prescription processing system correctness of the prescription request;
  preparing by said personnel a completed prescription form based on the submitted prescription request;
  sending the completed prescription form to a pharmacy;
  filling the prescription request, at the pharmacy, based on the completed prescription form;
  determining when the user would like to submit a new prescription request;
  repeating the steps of submitting, capturing, transcribing, preparing, sending, filling, and determining when the user would like to submit a new prescription request; and
  terminating the connection when the user would not like to submit a new prescription request.

59. A method of processing prescription requests comprising the steps:
  establishing a connection to a remotely located prescription processing system using a telephone;
  submitting an audible prescription request to the prescription processing system using said telephone, wherein the audible prescription request includes user information and a member ID number;
  capturing the prescription request;
  converting the captured prescription request to a digitized format to obtain a digitized prescription request;
  creating an identification file, including identification data, for the digitized prescription request;
  associating the identification file with the digitized prescription request to form a prescription file;
  storing the prescription file on a database maintained by the prescription processing system;
  transcribing the digitized prescription request;
  independently assessing by personnel associated with the prescription processing system correctness of the prescription request;
  preparing by said personnel a completed prescription form based on the submitted prescription request;
  sending the completed prescription form to a central pharmacy; and
  filling the prescription request, at the central pharmacy, based at least partially on the completed prescription form.

60. A method of submitting a prescription request for retrieval of a filled prescription by a patient, the method comprising the steps:
  initiating a connection to a remotely located prescription processing system using a telephone;
  submitting an audible prescription request to the prescription processing system using said telephone;
  capturing the audible prescription request;
  converting the captured prescription request to a digitized format to obtain a digitized prescription request;
  creating an identification file, including identification data, for the digitized prescription request;
  associating the identification file and the digitized prescription request to form a prescription file;
  storing the prescription file on a database maintained by the prescription processing system;
  transcribing the digitized prescription request;
  filling the prescription request, at a filling pharmacy responsive to receipt of the prescription request from the remotely located prescription processing system; and
  retrieving, by the patient, a filled prescription from a predetermined filling pharmacy remotely located from the prescription processing system.

61. A method of processing a submitted prescription request, comprising the steps:
  receiving a request from a remote source to establish a connection with a local prescription processing system;
  establishing a connection with the remote source using a telephone;
  receiving an audible prescription request by way of said telephone;
  capturing the audible prescription request;
  converting the captured prescription request to a digitized format to obtain a digitized prescription request;
  creating an identification file, including identification data, for the digitized prescription request;
  associating the identification file and the digitized prescription request to form a prescription file;
  storing the prescription file on a database maintained by the prescription processing system;
  transcribing the digitized prescription request;
  preparing, by a pharmacist, a completed prescription form based, at least partially, on the audible prescription request from the remotely located prescription processing system; and
  sending the completed prescription form to a pharmacy to be filled.

62. A method of processing prescription requests comprising the steps:
  establishing a connection to a remotely located prescription processing system;
  submitting a prescription request to the prescription processing system;
  capturing the prescription request;
  converting the captured prescription request to a digitized format to obtain a digitized prescription request;
  creating an identification file, including identification data, for the digitized prescription request;
  associating the identification file and the digitized prescription request to form a prescription file;
  storing the prescription file on a database maintained by the prescription processing system;
  transcribing the digitized prescription request;
  independently assessing by at least one of a pharmacist and personnel associated with the prescription processing system correctness of the prescription request;
  preparing, by said at least one of a pharmacist and personnel a completed prescription form based, at least partially, on the processed prescription request;

sending the completed prescription form to a filling pharmacy; and filling the prescription request, at the filling pharmacy, based at least partially on the completed prescription form, wherein said at least one of said pharmacist and said personnel and said filling pharmacy are remotely located front each other, and remotely located from said prescription processing system.

63. A method of processing prescription requests comprising the steps:

establishing a connection to a remotely located prescription processing system;

submitting a prescription request to the prescription processing system, wherein the prescription request includes user information and a member ID number;

capturing the prescription request;

converting the captured prescription request to a digitized format to obtain a digitized prescription request;

creating an identification file, including identification data, for the digitized prescription request;

associating the identification file with the digitized prescription request to form a prescription file;

storing the prescription file on a database maintained by the prescription processing system;

transcribing the digitized prescription request;

independently assessing by at least one of a pharmacist and personnel associated with the prescription processing system correctness of the prescription request, the at least one of the pharmacist and personnel and the prescription processing system being separate from at least one of a hospital and a physician where the prescription request was originated, and the at least one of the pharmacist and personnel and the prescription processing system being separate from a central pharmacy where the prescription request is to be fulfilled;

preparing, by said at least one of a pharmacist and personnel a completed prescription form based, at least partially, on the processed prescription request;

sending the completed prescription form to the central pharmacy; and filling the prescription request, at the central pharmacy, based at least partially on the completed prescription form wherein said at least one of said pharmacist and said personnel and said central pharmacy are remotely located from each other, and remotely located from said prescription processing system.

64. A method of processing prescription requests comprising the steps:

establishing a connection to a remotely located prescription processing system;

submitting a prescription request to the prescription processing system;

capturing the prescription request for subsequent manipulation;

transcribing the captured prescription request;

converting the captured prescription request to a digitized format at the prescription processing system to obtain a digitized prescription request;

storing the digitized prescription request on a database maintained by the prescription processing system;

creating an identification file, including identification data, for the digitized prescription request;

concatenating the identification file with the digitized prescription request to form a prescription file;

independently assessing by at least one of a pharmacist and personnel associated with the prescription processing system correctness of the prescription request, the at least one of the pharmacist and personnel and the prescription processing system being separate from at least one of a hospital and a physician where the prescription request was originated, and the at least one of the pharmacist and personnel and the prescription processing system being separate from a pharmacy where the prescription request is to be fulfilled;

preparing by said at least one of a pharmacist and personnel a completed prescription form based on the submitted prescription request;

comparing, at the prescription processing system, a physician's phone number and a prescription number;

if the physician's phone number and the prescription number result in a predetermined relationship, wherein the predetermined relationship is a match between the physician's phone number and the prescription number and a stored physician's phone number and a stored prescription number stored at the prescription processing system then filling the prescription request using an automated entry agent associated with the prescription processing system.

65. A method of processing prescription requests comprising the steps:

establishing a connection to a remotely located prescription processing system;

submitting a prescription request to the prescription processing system, wherein the prescription request is submitted by facsimile;

capturing the prescription request for subsequent manipulation;

transcribing the captured prescription request;

converting the captured prescription request to a digitized format at the prescription processing system to obtain a digitized prescription request;

storing the digitized prescription request on a database maintained by the prescription processing system creating an identification file, including identification data, for the digitized prescription request;

concatenating the identification file with the digitized prescription request to form a prescription file;

independently assessing by at least one of a pharmacist and personnel associated with the prescription processing system correctness of the prescription request, the at least one of the pharmacist and personnel and the prescription processing system being separate from at least one of a hospital and a physician where the prescription request was originated, and the at least one of the pharmacist and personnel and the prescription processing system being separate from a pharmacy where the prescription request is to be fulfilled;

preparing by said at lease one of a pharmacist and personnel a completed prescription form based on the submitted prescription request;

comparing, at the prescription processing system, a physician's phone number and a prescription number;

if the physician's phone number and the prescription number result in a predetermined relationship, wherein the predetermined relationship is a match between the physician's phone number and the prescription number and a stored physician's phone number and a stored prescription number stored at the prescription processing system then filling the prescription request using an automated entry agent associated with the prescription processing system.

66. A method of processing prescription requests comprising the steps:
- establishing a connection to a remotely located prescription processing system, wherein the step of establishing includes a step of establishing the connection using a telephone;
- submitting a prescription request to the prescription processing system, wherein the step of submitting includes communicating with the prescription processing system using a touch tone telephone keypad;
- capturing the prescription request for subsequent manipulation;
- transcribing the captured prescription request;
- converting the captured prescription request to a digitized format at the prescription processing system to obtain a digitized prescription request;
- storing the digitized prescription request on a database maintained by the prescription processing system;
- creating an identification file, including identification data, for the digitized prescription request;
- concatenating the identification file with the digitized prescription request to form a prescription file;
- independently assessing by at least one of a pharmacist and personnel associated with the prescription processing system correctness of the prescription request, the at least one of the pharmacist and personnel and the prescription processing system being separate from at least one of a hospital and a physician where the prescription request was originated, and the at least one of the pharmacist and personnel and the prescription processing system being separate from a pharmacy where the prescription request is to be fulfilled;
- preparing by said at least one of a pharmacist and personnel a completed prescription form based on the submitted prescription request;
- comparing, at the prescription processing system, a physician's phone number and a prescription number; and
- if the physician's phone number and the prescription number result in a predetermined relationship, wherein the predetermined relationship is a match between the physician's phone number and the prescription number and a stored physician's phone number and a stored prescription number stored at the prescription processing system then filling the prescription request using an automated entry agent associated with the prescription processing system.

67. A prescription processing system comprising:
- a telephone for receiving an audible prescription request;
- a computer for capturing the audible prescription request and for receiving a digitized prescription request, the computing creating an identification file, including identification data, for the at least one of the digitized prescription request and the audible prescription request and associating the identification file and the at least one of the digitized prescription request and the audible prescription request to form a prescription file;
- a header entry agent for retrieving general information from at least one of the digitized prescription request and the audible prescription request after the audible prescription request has been converted to a digitized format at the prescription processing system, and the general information is transcribed, and wherein said general information comprises non-medication related information comprising at least one of member's name, member's identification number, physician information, and patient information;
- a database for storing at least one of the digitized prescription request and the audible prescription request after the audible prescription request has been converted to a digitized format at the prescription processing system;
- a user interface enabling personnel associated with the prescription processing system to independently assesses correctness of at least one of the digitized prescription request and the audible prescription request and prepares a completed prescription form based on the at least one of the digitized prescription request and the audible prescription request; and
- a pharmacy for receiving said completed prescription form, and filling said prescription request based on the completed prescription form, and when the physician's phone number and the prescription number result in a predetermined relationship, wherein the predetermined relationship is a match between the physician's phone number and the prescription number and a stored physician's phone number and a stored prescription number stored at the prescription processing system then filling the prescription request, at the predetermined pharmacy, based on the completed prescription form.

68. The system of claim 67, wherein the header entry agent comprises at least one of a person or an intelligent software program.

69. The system of claim 67, wherein the personnel comprises at least one of a pharmacist, a medical doctor, and a licensed physician assistant.

70. The system of claim 67, wherein the digitized prescription request and the digitized format of the converted audible prescription request comprises at least one of ASCII, formatted text, Microsoft™ Word™, WordPerfect™, standard facsimile formats, standard wireless transmission formats, and standard digitized audio formats.

71. A method of processing prescription requests comprising the steps:
- establishing a connection to a remotely located prescription processing system using a telephone;
- submitting an audible prescription request to the prescription processing system using said telephone;
- comparing, at the prescription processing system, a physician's phone number and a prescription number; and
- if the physician's phone number and the prescription number result in a predetermined relationship, wherein the predetermined relationship is a match between the physician's phone number and the prescription number and a stored physician's phone number and a stored prescription number stored at the prescription processing system then filling the prescription request using an automated entry agent associated with the prescription processing system;
- capturing the audible prescription request;
- converting the captured prescription request to a digitized format to obtain a digitized prescription request;
- creating an identification file, including identification data, for the digitized prescription request;
- associating the identification file and the digitized prescription request to form a prescription file;
- storing the prescription file on a database maintained by the prescription processing system;
- transcribing the digitized prescription request;
- independently assessing by personnel associated with the prescription processing system correctness of the prescription request, said personnel comprising a non-physician user electronically signing a patient's orders resulting form said independently assessing;

preparing by said personnel a completed prescription form based on the submitted audible prescription request;

sending the completed prescription form to a filling pharmacy; and filling the prescription request, at the filling pharmacy, based at least partially on the completed prescription form;

prompting a user to input information associated with the prescription including requesting physician information; requesting user information; and requesting a member ID number;

determining if the prescription request is to renew an existing prescription or to submit a new prescription, and wherein when the prescription request is to submit a new prescription, and further comprises submitting member information; submitting patient information; and submitting medication information, and wherein when the prescription request is to renew a prescription and further comprises determining if there is an existing unique prescription number for renewal; and requesting the existing unique prescription number if it is available;

determining if there is a change in patient therapy that would affect one or more aspects of the prescription request; and if there is no change in patient therapy, then performing the steps reviewing the submitted prescription request to obtain the user's approval, and closing the prescription request;

if there is a change in therapy, then performing the steps of requesting new medication information from the user; and reviewing the new medication information;

if there is no prescription number for renewal, and further comprises requesting member information; requesting patient information; and requesting medication information;

determining if the user would like to submit a new prescription request;

repeating the steps of submitting, preparing, sending, and filling if the user would like to submit a new prescription request; and terminating the connection if the user would not like to submit an new prescription request.

* * * * *